(12) United States Patent
Gehrlein et al.

(10) Patent No.: US 7,075,645 B2
(45) Date of Patent: Jul. 11, 2006

(54) SPECTROSCOPIC ANALYZER FOR BLENDER

(75) Inventors: Lane Gehrlein, Pine Island, NY (US); Emil Ciurczak, Goldens Bridge, NY (US); Gary Ritchie, Kent, CT (US)

(73) Assignee: Euro-Celtique S.A. (LU)

( * ) Notice: Subject to any disclaimer, the term of this patent is extended or adjusted under 35 U.S.C. 154(b) by 330 days.

(21) Appl. No.: 10/426,980

(22) Filed: Apr. 30, 2003

(65) Prior Publication Data

US 2004/0019462 A1    Jan. 29, 2004

Related U.S. Application Data

(60) Provisional application No. 60/379,337, filed on May 9, 2002.

(51) Int. Cl.
*G01J 3/28* (2006.01)
*B01F 9/00* (2006.01)

(52) U.S. Cl. ............... 356/328; 356/419; 366/142; 366/143

(58) Field of Classification Search ............. 356/72, 356/326, 328, 419; 366/142, 143
See application file for complete search history.

(56) References Cited

U.S. PATENT DOCUMENTS

| | | | | |
|---|---|---|---|---|
| 3,416,864 A | * | 12/1968 | Keahl et al. | 356/332 |
| 4,054,389 A | * | 10/1977 | Owen | 356/419 |
| 5,859,708 A | * | 1/1999 | Feldman | 356/406 |
| 6,517,230 B1 | * | 2/2003 | Afnan et al. | 366/142 |

FOREIGN PATENT DOCUMENTS

| WO | WO 01/60503 A1 | * | 8/2001 |
|---|---|---|---|
| WO | WO 02/18912 A2 | * | 3/2002 |

* cited by examiner

*Primary Examiner*—F. L. Evans

(57) ABSTRACT

A blending apparatus comprises a blender including a container having a wall, the wall including a window. The container rotates about an axis of rotation. A wireless spectrometer is mounted to the container and operates through the window, in a direction that does not intersect the axis of rotation, for obtaining a set of spectroscopic data regarding the product during an operation of the blender. In addition, a method for assaying a blended product in a blender includes mounting a wireless spectrometer to the container, rotating the container about its axis of rotation so as to blend the product; operating the wireless spectrometer through a window in the container, in a direction that does not intersect the axis of rotation, to obtain spectroscopic data regarding the product during the blending, and determining a homogeneity of the product from the spectroscopic data.

80 Claims, 27 Drawing Sheets

SPECTROSCOPIC ANALYZER FOR BLENDER

This invention claims priority from U.S. Provisional Application No. 60/379,337 filed on May 9, 2002, the entire disclosure of which is hereby incorporated by reference.

FIELD OF THE INVENTION

The present invention relates to analyzing blended products. Specifically, the present invention relates to the use of a wireless spectrometer for determining a homogeneity of a product in a blender.

BACKGROUND OF THE INVENTION

Pharmaceutical raw materials may be fed into a mixing device, such as a blender, where the drug is mixed with other ingredients, generally non-pharmaceutically-active components known as excipients, in order to form a dosage form such as a tablet or capsule. During this process, the drug is mixed with suitable excipients such as dextrin, lactose, salt, polymers, celluloses, stearic acid, talc, or other inactive ingredients. The dosage unit can then be packaged as is, or it may be further modified into a more convenient form for administration to a patient, such as a capsule or tablet. A hopper may be used to feed the pharmaceutical raw material into the blender. A tableting or encapsulating machine may be used to form the capsule or tablet dosage form. Hoppers can also be used to feed the pharmaceutical raw material (which may be in the form of a granulate or dry blend) into a tableting/encapsulating machine.

When blending a product in a blender it is useful to know the homogeneity of the blended product in order to know when to end the blending process. Specifically, with regard to pharmaceutical products, it is important to be able to determine the homogeneity of the blended product with some precision in order to ensure that the proper dosage of the active drug is delivered to the patient and physical characteristics, such as dissolution, are consistent.

Vibrations that occur during the manufacturing process may cause stratification of the granules within the hopper prior to preparation of the dosage form. Stratification is localized areas of differing drug potencies, and may occur even though the composition within a localized area is itself homogeneous. Stratification may be related to varying particle size. A consequence of stratification may be a dosage form being prepared with an inaccurate dosage (e.g., a sub-potent or a super-potent product). Accordingly, the mixing of pharmaceutical compositions is a crucial step in processing an active drug into a dosage form.

Generally, the homogeneity of a pharmaceutical composition refers to the distribution of the active drug in the pharmaceutical composition, and the potency of a pharmaceutical composition refers to the amount of the active component in the pharmaceutical composition. Traditionally, the determination of the homogeneity and/or potency of a pharmaceutical mixture have been time consuming. In addition, traditional methods measure the homogeneity and potency only of the active component within a pharmaceutical composition and give no information concerning the homogeneity of the non-active components.

It is also important to determine the concentration of the other, non-active components within the pharmaceutical mixture. The concentration of the non-active components in a pharmaceutical mixture is important because it determines the physical properties of the mixture. For example, disintegrants affect the rate of dissolution of a tablet in a recipient's stomach. If the disintegrant is not homogeneously distributed in the pharmaceutical mixture, then the resulting tablets may not dissolve at a uniform rate, thereby potentially resulting in quality, dosing and bioavailability problems. Thus, it is important to measure the homogeneity of all the components of a pharmaceutical mixture because the dispersion of certain components may ultimately affect the physical properties of the final form of the pharmaceutical composition.

Additionally, as noted above, stratification may be associated with uneven distribution of particle size. The result may be quality, dosing and bioavailability problems.

Pharmaceutical products are typically mixed in a blender. Conventional blenders include, among others, "V"-blenders, ribbon blenders, and vertical blenders. According to one method for determining the homogeneity of a blended pharmaceutical product, a technician must stop the blender, remove samples of the blended product from various locations in the blender, and assay those samples in a laboratory using a technique such as ultra-violet (UV) spectroscopy or High Performance Liquid Chromatography (HPLC) analysis. While the samples are taken to the laboratory and analyzed, the blending process is put on hold. The analysis determines the potency of the product at each of the various locations. If the potency of each of the samples is the same (i.e., within statistical limits), then the mixture is determined to be homogeneous, and the blending process may end. However, neither UV nor HPLC analysis establishes the concentration of the non-active components of the mixture. If the potency is not the same for each of the samples, the blender is run again for a period and the testing is repeated.

Infrared spectroscopy is a technique which is based upon the vibrations of the atoms of a molecule. Transmitting radiation through a sample generates a spectrum determining what portion of the incident radiation is absorbed by the sample at a particular energy.

Infrared spectroscopy is a technique which is based upon the vibrational changes of the atoms of a molecule. In accordance with infrared spectroscopy, an infrared spectrum is generated by transmitting infrared radiation through a sample of an organic compound and determining what portion of the incident radiation are absorbed by the sample. An infrared spectrum is a plot of absorbence (or transmittance) against wave number, wavelength, or frequency. Infrared radiation (IR) may be roughly divided into three wavelength bands: near-infrared radiation, mid-infrared radiation, and far-infrared radiation. Near-infrared radiation (NIR) is radiation having a wavelength between about 750 nm and about 3000 nm. Mid-infrared radiation (MIR) is radiation having a wavelength between about 3000 and about 10,000 nm. Far-infrared radiation (FIR) is radiation having a wavelength between about 10,000 nm and about 1000 μm (1000 μm being the beginning of the microwave region). The desired range may be chosen to suit the analysis being performed.

In general, spectrometers (e.g., a spectrophotometer) can be divided into two classes: transmittance spectrometers and reflectance spectrometers. In a transmittance spectrometer, light having a desired narrow band of wavelengths is directed onto a sample, and a detector detects the light which was transmitted through the sample. In contrast, in a reflectance spectrometer, light having a narrow band of wavelengths is directed onto a sample and one or more detectors detect the light which was reflected from the sample.

Depending upon its design, a spectrometer may, or may not, be used as both a transmittance and a reflectance spectrometer.

A variety of different types of spectrometers are known in the art such as grating spectrometers, FT (Fourier transformation) spectrometers, Hadamard transformation spectrometers, AOTF (Acousto Optic Tunable Filter) spectrometers, diode array spectrometers, filter-type spectrometers, scanning dispersive spectrometers, and nondispersive spectrometers.

Filter-type spectrometers, for example, utilize a light source to provide continuous radiation (e.g. tungsten filament lamp) to illuminate a rotating opaque disk, wherein the disk includes a number of narrow bandpass optical filters. The disk is then rotated so that each of the narrow bandpass filters passes between the light source and the sample. An encoder indicates which optical filter is presently under the light source. The filters filter the light from the light source so that only a narrow selected wavelength range passes through the filter to the sample. Optical detectors are positioned to detect light which either is reflected by the sample (to obtain a reflectance spectra) or is transmitted through the sample (to generate a transmittance spectra). The amount of detected light is then measured, which provides an indication of the amount of absorbence of the light by the substance under analysis.

Diode source spectrometers use infrared emitting diodes (IREDs) as sources of near infrared radiation. A plurality of (for example, eight) IREDs are arranged over a sample work surface to be illuminated for quantitative analysis. Infrared radiation having a narrow bandwidth (e.g. 30–50 nm) emitted from each IRED impinges upon an accompanying optical filter. Each optical filter is a narrow bandpass filter which passes IR radiation at a different wavelength. IR radiation passing through the sample is detected by a detector (such as a silicon photodetector). The amount of detected light is then measured, which provides an indication of the amount of the substance under analysis, based upon absorbence of the light.

Acousto Optical Turnable Filter spectrometers utilize an RF signal to generate acoustic waves in a $TeO_2$ crystal. A light source transmits a beam of light through the crystal, and the interaction between the crystal and the RF signal splits the beam of light into three beams: a center beam of unaltered white light and two beams of monochromatic and orthogonally polarized light. A sample is placed in the path of one of the monochromatic beam detectors, which are positioned to detect light which either is reflected by the sample (to obtain a reflectance spectra) or is transmitted through the sample (to generate a transmittance spectra). The wavelength of the light source is incremented across a wavelength band of interest by varying the RF frequency. The amount of detected light is then measured, which provides an indication of the amount of absorbence of the light by the substance under analysis.

In an ATR (attenuated total reflectance) spectrometer, radiant energy incident on an internal surface of a high refractive index transparent material is totally reflected. When an infrared absorbing material is in optical contact with the totally internally reflecting surface, the intensity of the internally reflected radiation is diminished for those wavelengths or energies where the material absorbs energy. Since an internal reflecting surface is essentially a perfect mirror, the attenuation of this reflected intensity by a material on its surface provides a means of producing all absolution spectrum of the material. Such spectra are called internal reflection spectra or attenuated total reflection (ATR) spectra. An ATR spectrometer, as described herein, refers to any type of spectrometer (e.g., grating, FT, AOTF, filter) which includes, as a component part, an ATR crystal.

The material with the high index of refraction that is used to create internal reflection is called an internal reflection element (IRE) or an ATR crystal. The attenuation of the internally reflected radiation results from the penetration of the electromagnetic radiation field into the matter in contact with the reflection surface. This field was described by N. J. Hayrick (1965) as an evanescent wave. It is the interaction of this field with the matter in contact with the IRE interface that results in attenuation of the internal reflection.

In granting monochromator spectrometers, a light source transmits a beam of light through an entrance slit and onto a diffraction grating (the dispersive element) to disperse the light beam into a plurality of beams of different wavelengths (i.e., a dispersed spectrum). The dispersed light is then reflected back through an exit slit onto a detector. By selectively altering the path of the dispersed spectrum relative to the exit slit, the wavelength of the light directed to the detector can be varied. The amount of detected light is then measured, which provides an indication of the amount of absorbence of the light by the substance under analysis. The width of the entrance and exit slits can be varied to compensate for any variation of the source energy with wave number.

Detectors used in spectroscopy generally fall into two classes, photographic detectors, in which radiation impinges upon an unexposed photographic film, and electronic detectors, in which the radiation impinges upon a detector and is converted into an electrical signal. Electronic detectors provide the advantage of increased speed and accuracy, as well as the ability to convert the spectral data into an electronic format, which can be displayed, processed, and/or stored. Examples of electronic detectors include photomultiplier tubes and photodetectors. Photomultiplier tubes are quite sensitive, but are relatively large and expensive. Photodetectors provide the advantage of reduced size and cost. Some examples of photodetectors are pin diode detectors, charge coupled device detectors, and charge injection device detectors.

U.S. Pat. No. 5,946,088, which is incorporated by reference herein, purportedly describes an apparatus for mixing compositions into a homogeneous mixture using a blender and detecting on-line the homogeneity and potency of the mixture using a spectrometer. In a preferred embodiment, a "V"-blender is described, which mixes compositions, such as powders or liquids, in a "V"-shaped container by rotating the container about a horizontal axis of rotation. Two support shafts, which connect to the container along its axis of rotation, support the container and drive the rotation of the container about the axis. The wall of the container includes a single aperture at the location in the wall intersecting the axis of rotation of the container. One of the support shafts connects to the container precisely at the point of the aperture and forms a seal for the aperture. The support shaft forming the seal for the aperture is hollow with a transparent window covering its end where it contacts the aperture. A detection means, which includes a fiber optic bundle for detecting the spectroscopic characteristics of the composition mixture is rotatably mounted through the inside of the hollow support shaft. At one end, the optical fibers abut against the transparent window on the inside of the hollow support shaft. At the other end, at a location remote from the "V"-blender, the fibers attach to a spectroscopic means. Thus, the spectrometer and fiber optic bundle remain stationary, while the support shaft and the transparent widow, rotate relative to them. This apparatus, with the fiber optic, bundle threaded through the rotating hollow support shaft, enables the spectrometer to acquire spectroscopic information about the composition mixture while the container is rotating about its axis, and thus, while the product is being blended.

SUMMARY OF THE INVENTION

The apparatus described in U.S. Pat. No. 5,946,088 has several disadvantages. Inaccurate results can be yielded because the measuring of data occurs at only one single fixed point on the rotating "V"-blender—the intersection of the wall and the axis of rotation. Furthermore, the apparatus is complex, difficult to construct, and expensive. The blender must be specially constructed with a single aperture precisely at the point that the blender wall intersects with one of the rotating shafts. The shaft must be bored out, and a transparent window sealed to one end. Expensive fiber optic cable must be rotatably mounted inside the shaft so as to remain stationary while the shaft and transparent window rotate relative to it. Because the radiation must pass twice through a window that is moving relative to the fibers, any optical imperfections in the window can cause further inaccuracies in the data collected. Vibrations of the rotating shaft and window can also distort the data. Moreover, the apparatus has inherent mechanical and structural disadvantages. The surface of the shaft and window that form a tight seal with the wall of the container, is precisely the same surface which both supports the container, and drives a high-speed rotation of the container. These forces can cause leaks in the seal.

Moreover, prior art devices use infrared spectrometers that transmit their data measurements of the molecular composition of pharmaceuticals by a physical connection, rather than by a wireless one. Thus, such spectrometers remain physically connected to devices that interpret the data and to devices that contain the pharmaceutical mixtures. The necessity of such a physical connection increases the number of devices necessary to analyze the spectral data and increases the complexity of the device that prepares the pharmaceutical dosage form.

In wireless transmissions of data, i.e., when the transmission of data does not use a physical connection (such as copper cable or fiber optics), electromagnetic radiation is useful to transmit information over long distances without damaging the information due to noise and interference. Various techniques for digital transmission of data are known in the art. Typically, the desired information is encoded into a digital signal and then may be modulated onto a carrier wave and made part of a larger signal. The signal is then sent into a multiple-access transmission channel, and electromagnetic radiation, e.g., radio, infrared, and visible light, is used to send the signal. After, transmission, the above process is reversed at the receiving end, and the information is extracted. Wireless data transmission may be, for example, via radio waves or via visible, IR or NIR optical link. Examples of wireless data transmission via visible or NIR optical link include remote controls for television and wireless data ports of laptop computers and personal digital assistants (PDAs). Examples of wireless data transmission via radio waves include cellular phones, wireless LAN and microwave transmission.

None of the prior art systems provide an apparatus for wirelessly determining the homogeneity aid potency of the components of a pharmaceutical mixture in a blender. Accordingly, it is desirable to provide an apparatus that can assess the homogeneity and potency of the components of a pharmaceutical mixture, detect stratification or non-uniformity of the mixture of the components prior to preparation of the dosage form from the pharmaceutical mixture, and transmit this information wirelessly to a computer for analysis.

The present invention provides an apparatus for blending a product that includes a blender including a container having a wall including a window, the container rotating about all axis of rotation. A wireless spectrometer is mounted to the container and operates through the window, in a direction that does not intersect with the axis of rotation, for obtaining a set of spectroscopic data regarding the product during an operation of the blender. The wireless spectrometer may be mounted to the window.

The spectrometer may be a near infrared spectrometer. The apparatus may also include a remote processing device in communication with the spectrometer, and the spectrometer may communicate with the remote processing device during operation of the blender. The remote processing device may calculate a value indicative of the homogeneity and/or stratification of the product, and may end an operation of the blender when the calculated value reaches a predetermined value. The spectrometer may receive calibration information from the remote processing device before obtaining spectroscopic data. The product being mixed in the blender may be a powder mixture.

The window may be an elongated window and the wireless spectrometer may be capable of being repositioned along the window for obtaining spectroscopic data a various positions on the container.

A second window and a second wireless spectrometer may also be provided, each mounted on the container, the second window also disposed in the wall so as not to intersect with the axis of rotation.

The present invention further provides all apparatus for blending a product in a blender, the blender including a container having a wall. First and second windows are disposed in the wall, and first and second wireless spectrometers mounted on the container operate through the first and second windows, respectfully, for obtaining first and second sets of spectroscopic data regarding the product. The first wireless spectrometer may be mounted to the first window and the second wireless spectrometer may be mounted to the second window.

The present invention further provides a method for assaying a blended product in a blender, the blender including a container having a wall and an axis of rotation, the wall including a window. A wireless spectrometer is mounted to the container; the container is rotated about its axis of rotation so as to blend the product; the wireless spectrometer is operated through the window, in a direction that does not to intersect with the axis of rotation, to obtain spectroscopic data regarding the product during the blending; and a homogeneity of the product is determined from the spectroscopic data.

As inn the apparatus, the spectrometer may be a near infrared spectrometer, and the spectrometer may be mounted to the window. The window may be an elongated window, and the wireless spectrometer may be repositioned along the window for obtaining spectroscopic data a various positions on the container. The homogeneity may be determined during the blending. The spectroscopic data may be transmitted to a remote processing device and the transmission may be during the blending of the product. The remote processing device may determine the homogeneity of the product. The method may also include downloading calibration information from the remote processing device to the spectrometer, and may also include stopping the blender when the homogeneity of the product reaches a predetermined value.

The present invention further provides a method for assaying a blended product in a blender, the blender including a container having a wall and first and second windows disposed in the wall. The product is blended in the blender; first and second wireless spectrometer are operated through the respective first and second windows to obtain a respective first and second sets of spectroscopic data regarding the product; and a homogeneity of the product is determined from the first and second sets of spectroscopic data.

In accordance with certain embodiments of the present invention, the spectrometer comprises at least one linear variable filter moved by a translating device such as a piezoelectric bimorph relative to a light source, such that said mixture in the hopper is irradiated with radiation in at least one specified band of wavelengths corresponding to the position of said at least one linear variable filter relative to said light source. In accordance with other aspects of this embodiment, the at least one variable filter includes a plurality of variable filters, and the detector includes a plurality of individual detectors, each of the plurality of variable filters passes light in a different band of wavelengths, each of the plurality of variable filters being associated with a corresponding one of the plurality of detectors.

BRIEF DESCRIPTION OF THE DRAWINGS

Similar elements are numbered similarly in the Figures.

DETAILED DESCRIPTION

Figure 1:
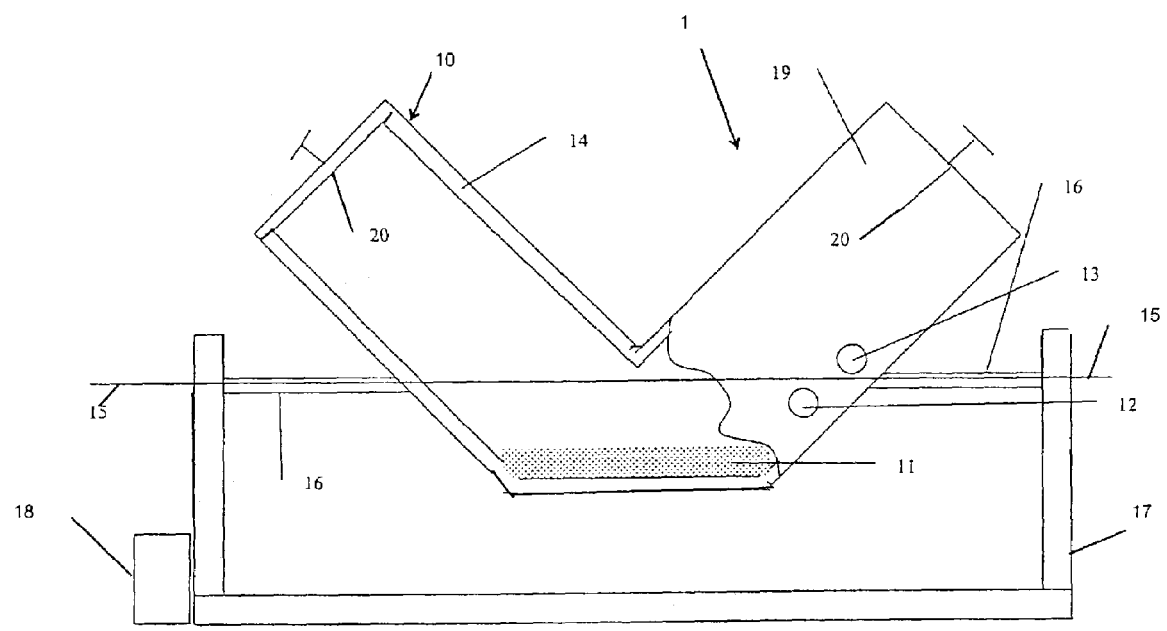
FIG. 1 shows a schematic view of a exemplary embodiment of a blending apparatus according to the present invention.

FIG. 1 shows a schematic view of a exemplary embodiment of blending apparatus 1 of the present invention. Blending apparatus includes "V"-blender 10 including container 19 having wall 14. Container 19 has a general "V"-shape formed by two hollow legs. Openings 20 at the top of each hollow leg may be used for inserting individual compositions of matter into blender 10 to be mixed together into product 11, or for removing product 11 when the blending process has completed. Shafts 16 defining axis 15, rotatably supported by support frame 17, provide support for container 19 and enable container 19 to rotate about axis 15 so that axis 15 forms the axis of rotation of container 19. Blender driver 18 is operationally connected to one or both of shafts 16 and provides a motive force to shafts 16 to rotate container 19 about axis 15. The rotation of container 19 causes the individual compositions of matter inside container 19 to tumble about within container 19, therefore mixing with each other to form product 11 Upon sufficient revolutions of container 19 product 11 will eventually become a homogenous mixture. The mixture may, for example, be a dry blend or a granulate.

It should be appreciated that although the embodiments of the present invention are described herein in connection with a V-blender, other types of blenders can alternatively be used, including, for example, ribbon blenders, vertical blenders, and the like.

Container 19 also includes first window 12 and second window 13 disposed in wall 14. The embodiment shown in FIG. 1 includes two windows as an example. More or fewer windows may be disposed in wall 14. First and second windows 12 and 13 may be located anywhere in wall 14, however they should not be located in wall 14 so as to intersect with axis 15 and thus complicate construction and operation of blending apparatus 1. Preferably, first and second windows should be located a sufficient distance away from axis 15 so that wireless spectrometers may operate through first and second windows without shafts 16 interfering with that operation. First and second wireless spectrometers mounted on container 19 for operating through first and second windows 12 and 13 are not shown in FIG. 1.

Figure 2A:
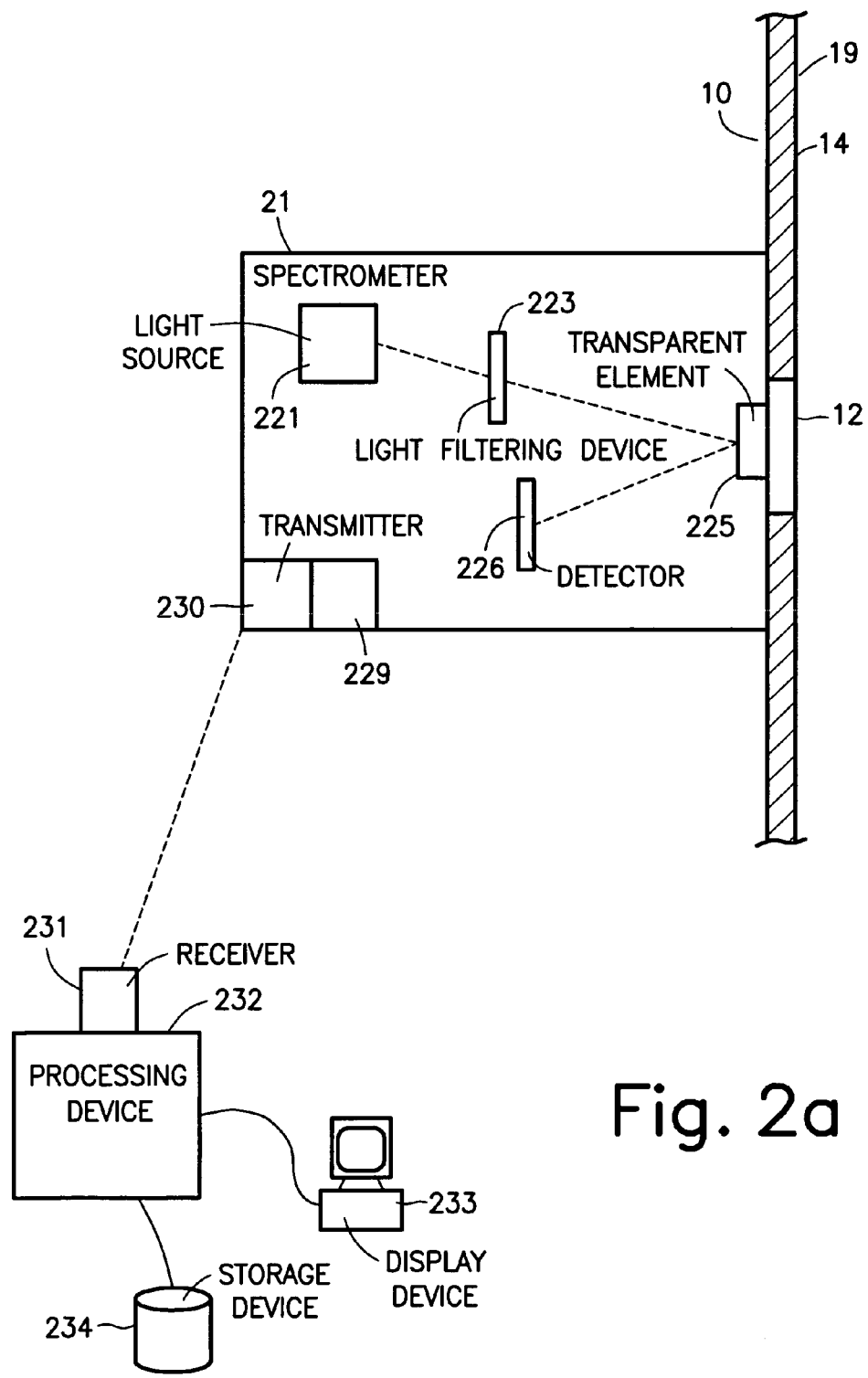
FIG. 2A shows a schematic representation of a first embodiment of a spectrometer in a pre-dispersive configuration.

FIG. 2A shows a detailed schematic view of a first embodiment of spectrometer 21 mounted on container 19 for operating through first window 12. Spectrometer 21 may be mounted to first window 12. The same or another spectrometer may also be mounted on container 19 for operating through second window 13. This spectrometer may be mounted to second window 13. As discussed above, a variety of different types of spectrometers are known in the art, such as grating spectrometers, FT (Fourier transformation) spectrometers, Hadamard transformation spectrometers, AOTF (Acousto Optic Tunable Filter) spectrometers, diode source spectrometers, filter-type spectrometers, scanning dispersive spectrometers, nondispersive spectrometers, and others as discussed below, and any of these may be used with the present invention.

In applications in which an ATR spectrometer is used, it may be helpful, though not absolutely necessary, to place pressure on an IRE (e.g., the ATR crystal) to improve performance by increasing the amount of the substance (e.g. product 11) that is in contact with the IRE. Pressure may be generated by placing the IRE in a lower region of blender 10, where higher pressure exists due to the weight of product 10 above. Alternatively, the IRE may be mounted on a piston device that presses into product 10 when in a forward position so that the spectrometer only scans when in this forward position.

Spectrometer 21 in FIG. 2A has a light source 221, a light filtering device 223, a transparent element 225 and a detector 226. Light source 221 generates a beam of light or radiation that passes through light filtering device 223. Light filtering device 223 separates the beam of polychromatic light into a monochromatic beam (or a beam having a narrower band of wavelengths than the polychromatic beam that is generated by light source 221 has), which then passes through a transparent element 225, such as a lens, that is set within or adjacent to window 12 in wall 14 of container 19, as illustrated in FIG. 2A. After passing through transparent element 225, the beam of light or radiation impinges on product 11 (not shown in FIG. 2A) inside container 19. The reflected light is then absorbed by detector 226, which converts the beam of radiation into a digital signal. In an embodiment of the present invention utilizing an ATR spectrometer, the transparent element 225 may be the IRE and the beam could reflect off the interface between product 11 and spectrometer transparent element 225 (e.g., where the product 11 and transparent element 225 contact one another). This configuration of the embodiment of FIG. 2A is "pre-dispersive" because the light generated by light source 221 passes through light filtering device 223 and is filtered to a monochromatic beam prior to it being dispersed by or reflected off the substance being analyzed, i.e., product 11.

In certain embodiments, detector 226 can be a photographic plate, a photoemissive detector, an imaging tube, a solid-state detector or any other suitable detector. Light filtering device. 223 can be a prism, a grating filter (which is an optical device with a surface ruled with equidistant and parallel lines for the purpose of filtering light), an interferometer, a filter wheel, linear variable filter, or any other suitable filter. In an FTIR embodiment, a beam splitter and a movable mirror can be incorporated into spectrometer 21.

Preferably, spectrometer 21 and transparent element 225 are located at a position adjacent to window 12 or at a position adjacent to window 13, as shown in FIG. 1, or elsewhere suitable. Wherever spectrometer 21 is located, embodiments utilizing a single spectrometer can be useful for collecting spectra from product 11 as it passes by transparent element 225. The spectra collected over time can be compared with each other to identify spectral differences in product 11 indicative of nonhomogeneity.

The material for transparent element 225 can be selected as a function of the desired wavelength to be used. For example, glass is transparent up to 2200 nm, saffire is transparent up to 5 microns, and barium fluoride is transparent up to 20 microns.

In this embodiment, as illustrated in FIG. 2A, spectrometer 21 is in wireless communication with a remote processing device 232 such that spectrometer 21 is capable of wirelessly transmitting spectral data to remote processing device 232 at a remote location. In one embodiment, detector 226 converts the reflected beam into a digital signal that is then wirelessly transmitted to remote processor 232, where the reflected beam is analyzed. The digital signal generated by detector 226 of spectrometer 21 is first fed into a transmitter 230 located in or attached to spectrometer 21 and coupled to detector 226. Transmitter 230 then transmits the digital signal wirelessly to a receiver 231, which receives the digital signals on behalf of processing device 232. The digital signal can be transmitted from transmitter 230 to receiver 231 by any known technique in the wireless transmission art, as will be discussed in greater detail below. Blender driver 18 (shown in FIG. 1) may also be in communication with processing device 232 either through a wireless or a physical (e.g. copper wire) connection.

Figure 2B:
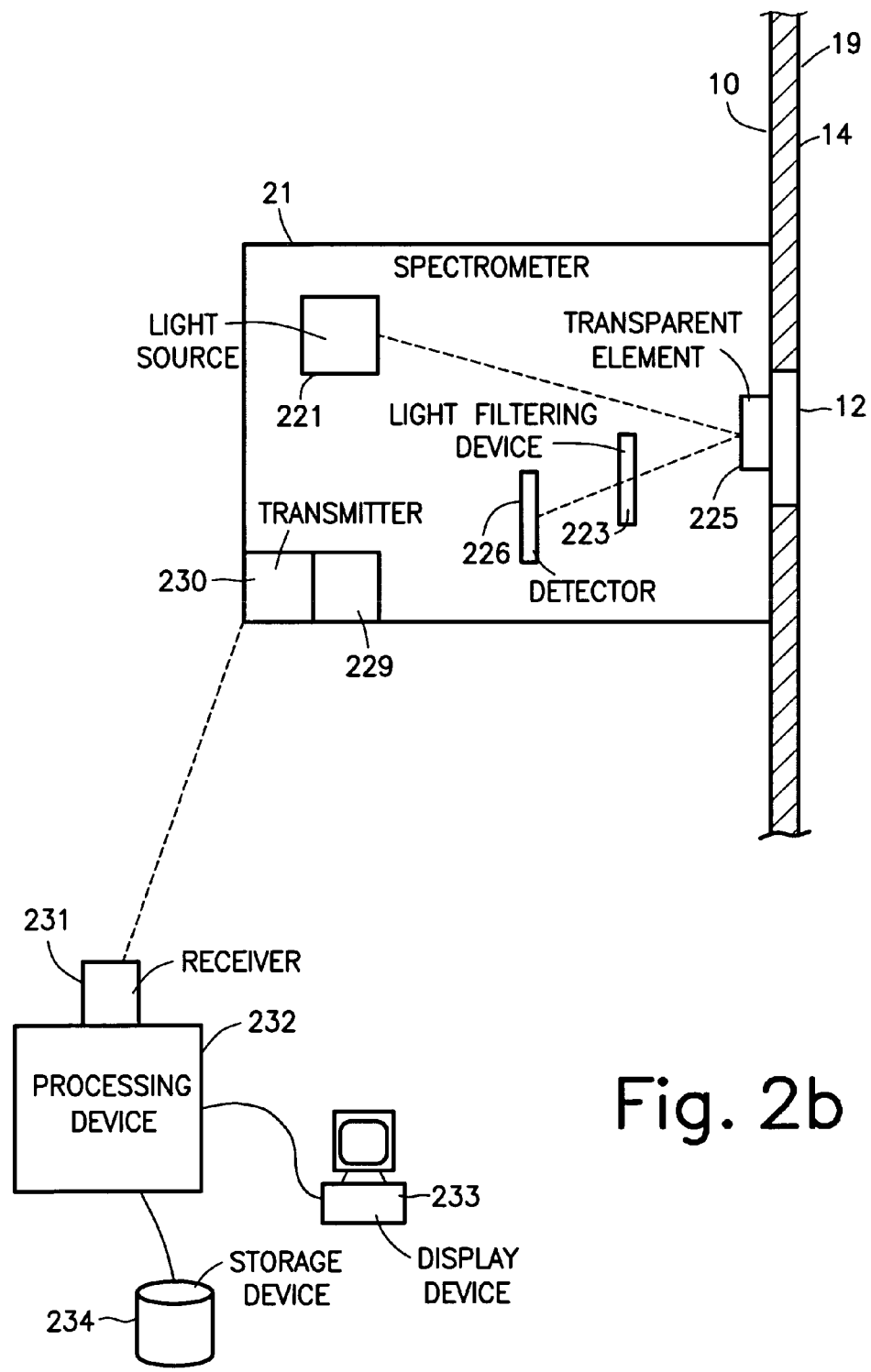
FIG. 2B illustrates a schematic representation of a first embodiment of spectrometer in a post-dispersive configuration.

FIG. 2B illustrates a schematic representation of the first embodiment of the invention in a post-dispersive configuration. In this embodiment, the beam of light generated by light source 221 first impinges upon product 11 and only then passes through light filtering device 223. After passing through light filtering device 223, the reflected light is absorbed by detector 226. This configuration is "post-dispersive" because the light generated by light source 221 passes through light filtering device 223 and is filter to a monochromatic beam (or a beam having a narrower band of wavelengths than the polychromatic beam that is generated by light source 221 has) after is has been dispersed by or reflected off the substance being analyzed, i.e., product 11.

Figure 2C:
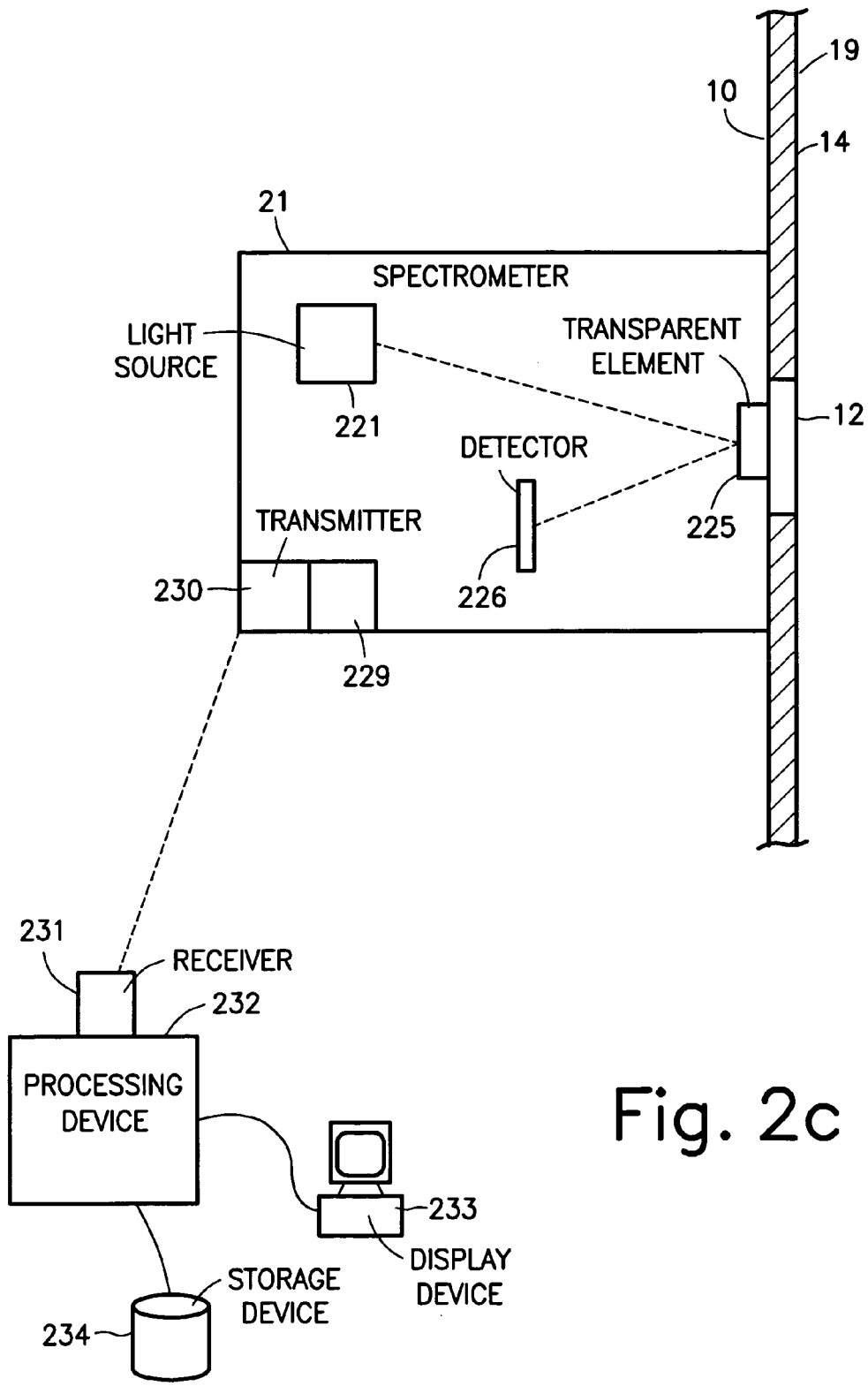
FIG. 2C illustrates a schematic representation of a first embodiment of a spectrometer in a configuration that uses a monochromatic source of light and no filter.

FIG. 2C illustrates a schematic representation of the first embodiment of the invention in a configuration wherein spectrometer 21 does not comprise a light filtering device 223 at all. In this embodiment, because light filtering device 223 is not present, light generated by light source 221 is not passed through a filtering device either prior to being reflected off product 11 or after being reflected off product 11. Instead, light source 221 itself generates a beam of monochromatic light. Light source 221 can thus be for example, a monochromatic laser.

Figure 2D:
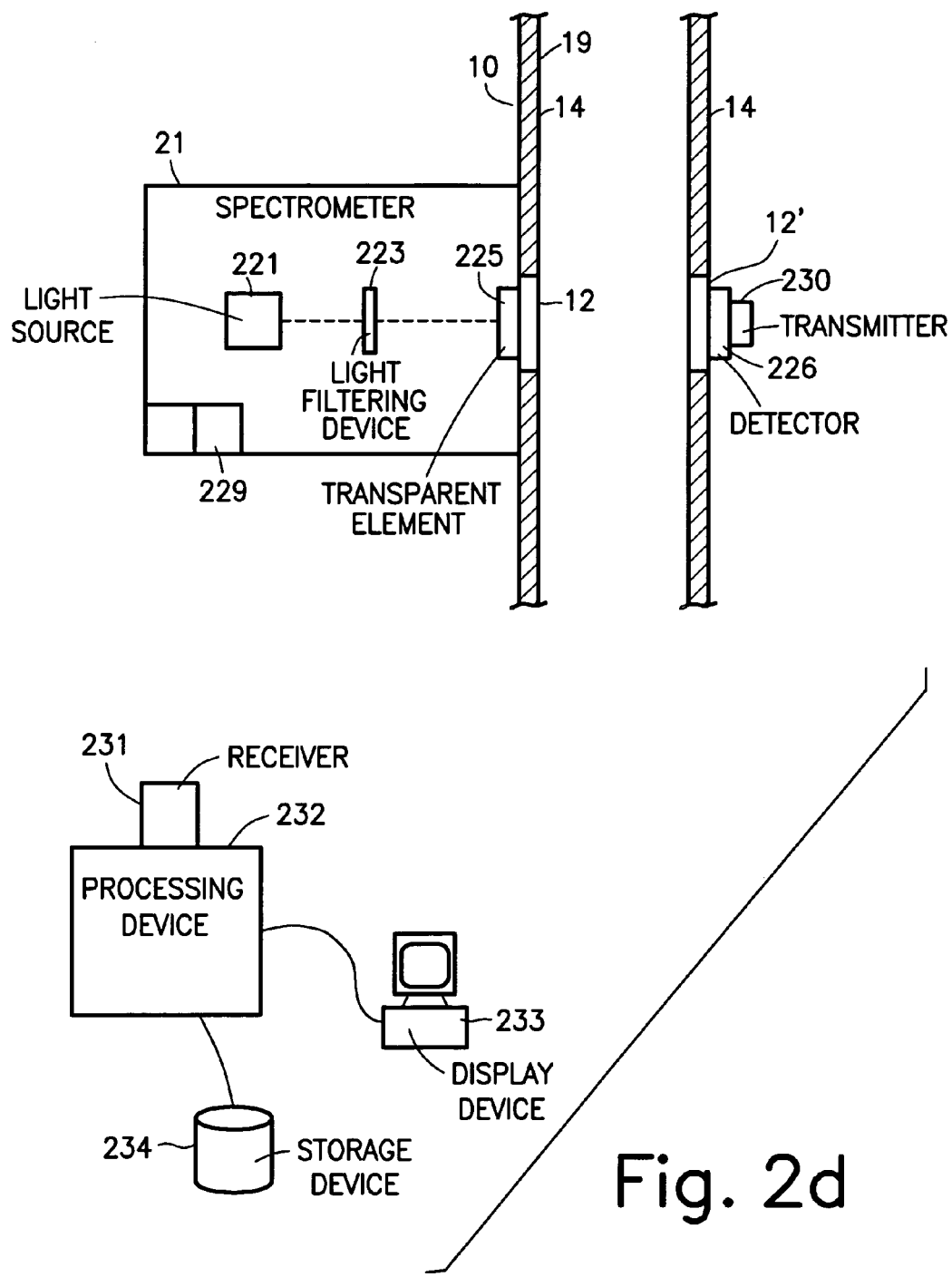
FIG. 2D illustrates a schematic representation of a first embodiment of a spectrometer wherein the light source and detector are configured for a transmittance measurement.

FIG. 2D illustrates a schematic representation of a first embodiment of the invention wherein light source 221 and detector 226 of spectrometer 21 are configured for a transmittance measurement. Light source 221 generates a beam of light, which passes through light filtering device 223 and onto product 11. Transparent element 225, can also be included within this configuration, in order to focus or direct light onto product 11. The beam of light then impinges detector 226, where the spectral data is measured. Alternatively, filtering device 223 could be situated adjacent to detector 226 (not shown), rather than adjacent light source 221, so that filtering of the light beam is performed post-dispersively, rather than pre-dispersively, as shown in FIG. 2D. Detector 226 can be situated inside wall 14 of container 19 (not shown) or outside wall 14, in which case light would exit container 19 through window 12' directly across the container from window 12. Whether light filtering device 223 is located adjacent to light source 221 or to detector 226, filtering device 223 and/or transparent element 225 could alternatively form a portion of wall 14 of container 19. In this embodiment, detector 226 may communicate with transmitter 230 or processing device 232 by a physical connection (e.g., a copper wire) or wirelessly, as discussed below.

Figure 2E:
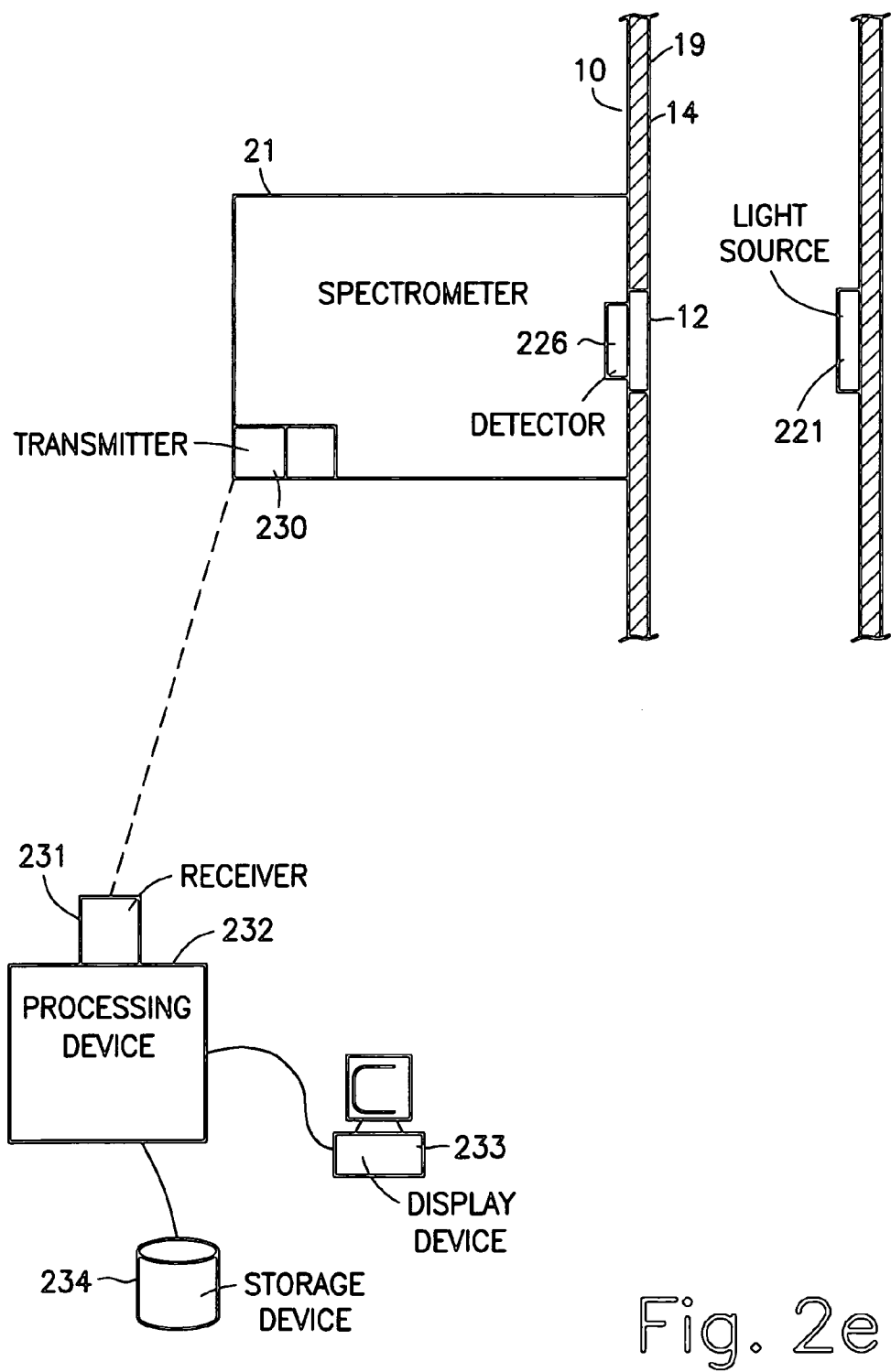
FIG. 2E shows a schematic representation of a first embodiment of a spectrometer wherein the light source and detector are mounted inside the blender.
Figure 2F:
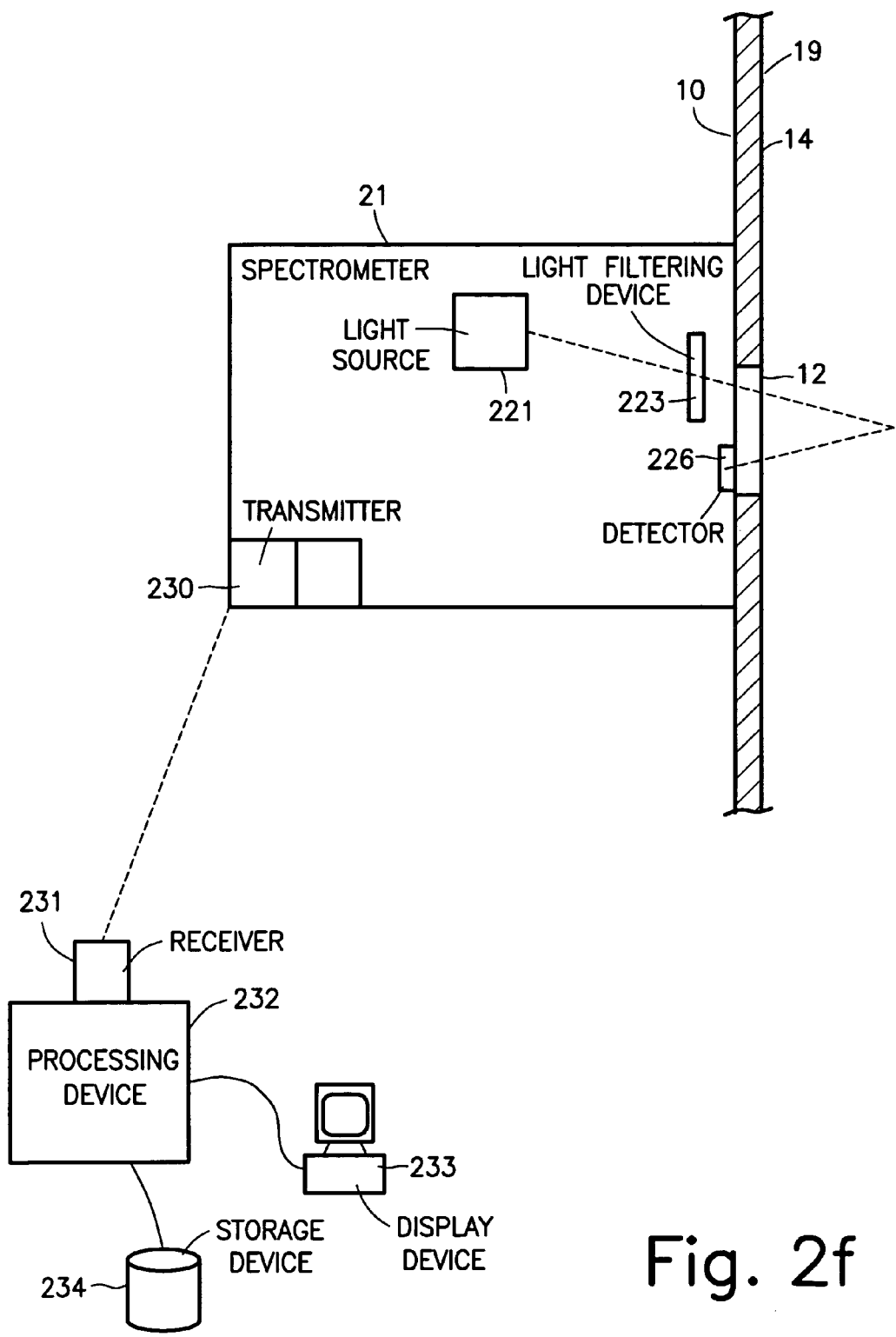
FIG. 2F shows a schematic representation of a first embodiment of a spectrometer wherein the light source and detector are configured for a reflectance measurement.

FIG. 2E shows an embodiment of the invention in a variation of FIG. 2D wherein the positions of light source 221 and detector 226 are effectively reversed. In this embodiment, light source 221 is still situated on the opposite side of container 19 from detector 226 in order to facilitate transmittance spectrometry. As shown in FIG. 2E, however, detector 226 is located adjacent to spectrometer 21. As shown in FIG. 2E, detector 226 may be mounted outside of wall 14 of container 19 within spectrometer FIG. 2F shows a schematic representation of an embodiment of the invention in a side view of container 19, wherein light source 221 and detector 226 are configured for a reflectance measurement. Light source 221 generates a beam of light, which passes through light filtering device 223 and onto product 11. A portion of the beam of light reflected off the product 11 continues onto detector 226, where the spectral data is measured.

Figure 2G:
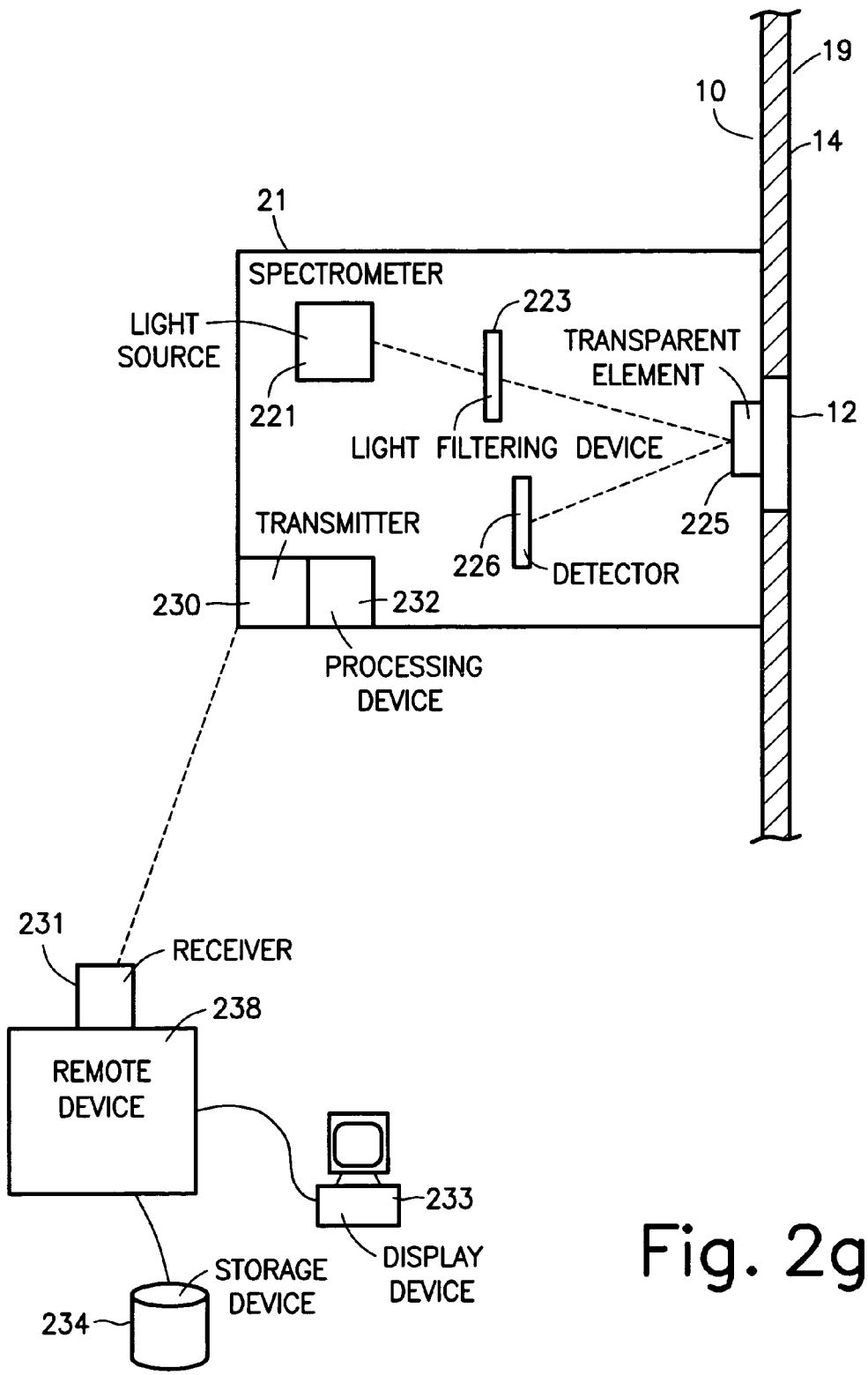
FIG. 2G shows a schematic representation of a second embodiment of a spectrometer in a mode wherein the processing device is physically connected to spectrometer.

FIG. 2G illustrates a second embodiment of the invention in a mode wherein processing device 232 is physically connected to spectrometer 21, rather than being remotely separated therefrom, as shown in FIGS. 2A–2F. In this embodiment, detector 226 converts the reflected beam into a digital signal that is then transmitted to processor 232 that is physically within, attached to or adjacent to spectrometer 21, where the reflected beam is analyzed. The connection between processing device 232 and detector 226 can be by conventional cables, wires or data buses, in which case transmission takes place through such physical connections. In this embodiment, there is no need for the digital signal generated by detector 226 to be fed in to a transmitter located in or attached to spectrometer 21 and then transmitted wirelessly to a receiver on behalf of processing device 232.

However, a transmitter 230 may still be present and located in or attached to spectrometer 21 and coupled to processor 232. The digital signal that is analyzed and/or transformed by processing device 232 can be then fed to transmitter 230 for transmission to receiver 231 via a wireless connection. Transmitter 230 transmits the digital signal of data processed by processing device 232 wirelessly to receiver 231, which receives the digital signals on behalf of a remote device 238 for further processing. As before, the digital signal can be transmitted from transmitter 230 to receiver 231 by any known technique in the wireless transmission art, as will be discussed in greater detail below. Processing device 232 may compress the digital signal so that it can be transmitted more efficiently or may modify the digital signal to facilitate error correction/detection, such as by inserting hamming code bits or error checking bits into the digital signal. The receiver can be physical connected to other devices (e.g., another processing device or display device).

Figure 3:
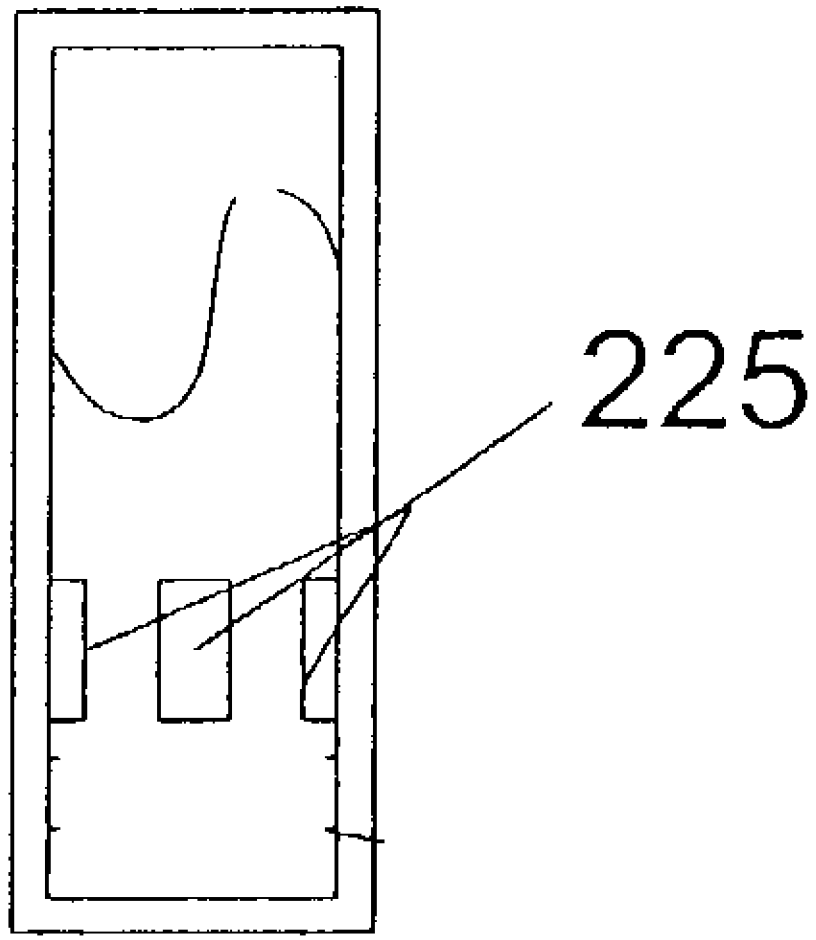
FIG. 3 shows a schematic representation of a third embodiment of the present invention wherein a plurality of spectrometers or transparent elements are used.

FIG. 3 shows a third embodiment of the invention wherein a plurality of transparent elements 225 are disposed about the circumference of container 19. In this embodiment, each transparent element 225 can be optically connected to a separate spectrometer 21. Thus, spectroscopic scans of the composition at different positions or angles in container 19 can be taken. In this embodiment, each of the plurality of spectrometers 21 situated about the circumference of container 19 can be any of the embodiments discussed above, and as shown in FIGS. 2A–2G, or as discussed below. Thus, the various spectrometers can derive data regarding product 11 through may variations and embodiments, so as to obtain readings that are verifiably accurate though various different techniques.

Figure 4:
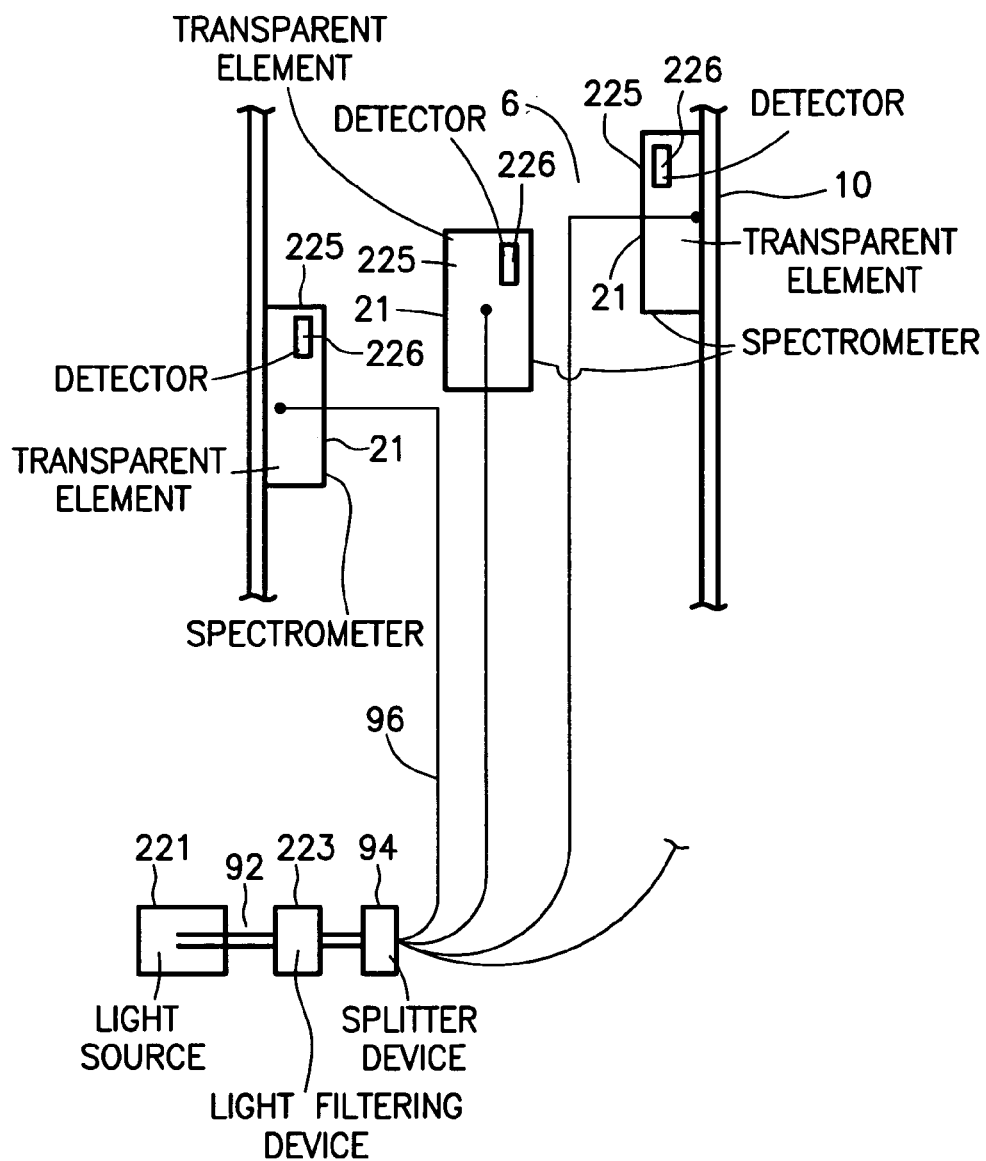
FIG. 4 shows a schematic representation of an embodiment of the present invention wherein a fiber optic bundle is used as a light source for illuminating multiple positions.

With further reference to FIG. 3 and FIGS. 1A and 1B, in an embodiment of the present invention, plurality of spectrometers 21 may be located in a region of blender 10, so that light sources 221 flood the region with large amounts of light. A "ring of light" may thus be provided. Large amounts of light provide a relatively large signal-to-noise ratio for spectral analysis purposes. Such an embodiment would be especially useful for analyzing the homogeneity of product 11. Light sources 221 could be NIR light emitting diodes (LEDs), for example, since such devices generate relatively little heat. Detectors 226 for each spectrometer 21 may be diode arrays or linear variable filter detectors (such as the MicroPac family of products available from OCLI), for example. Alternatively, detectors 226 could each include a number of individual diodes having a respective filter 223 for excluding all but a desired wavelength of light, as in the embodiment shown in FIG. 1B. In this way, intensity values at different wavelengths may be measured for each position on blender 10. In other embodiments or the present invention, a fiber optic bundle split into individual optical fibers, as shown in FIG. 4 below, could be used as the light source for flooding the desired region with light FIG. 4 shows another embodiment of the invention wherein a plurality of spectrometers 21 or transparent elements 225 are disposed about the circumference of blender 10. This embodiment may be especially useful for analyzing for stratification in blender 10. In this embodiment, light source 221 includes fiber optic bundle 92 optically connected to filtering, or monochromator, device 223. Filtering device 223 may be a grating, interferometer, filter wheel, or other suitable device for producing a monochromatic beam of light in each fiber of fiber optic bundle 92. Splitter device 94 is provided for splitting fiber optic bundle 92 into a plurality of individual fibers 96, which illuminate respective multiple positions, or angles, in blender 10 via respective transparent elements 225. In applications in which the blender housing rotates (such as in a V-blender), components 21, 92, 223, and 94 are preferably secured to the rotating blender housing (e.g. container 19 of FIG. 1 in the case of a V-blender). Respective detectors 226 are provided at each position or angle in blender 10 for detecting light diffusively reflected, transmitted, etc., from product 11. Any desired number of spectrometers 21, and hence, of illumination and detection (sampling) positions on blender 10, may be provided situated in a desired configuration about the circumference of the blender. Moreover, the spectrometers may be positioned at different longitudinal levels on blender 10, as shown in FIG. 4.

Figure 5:
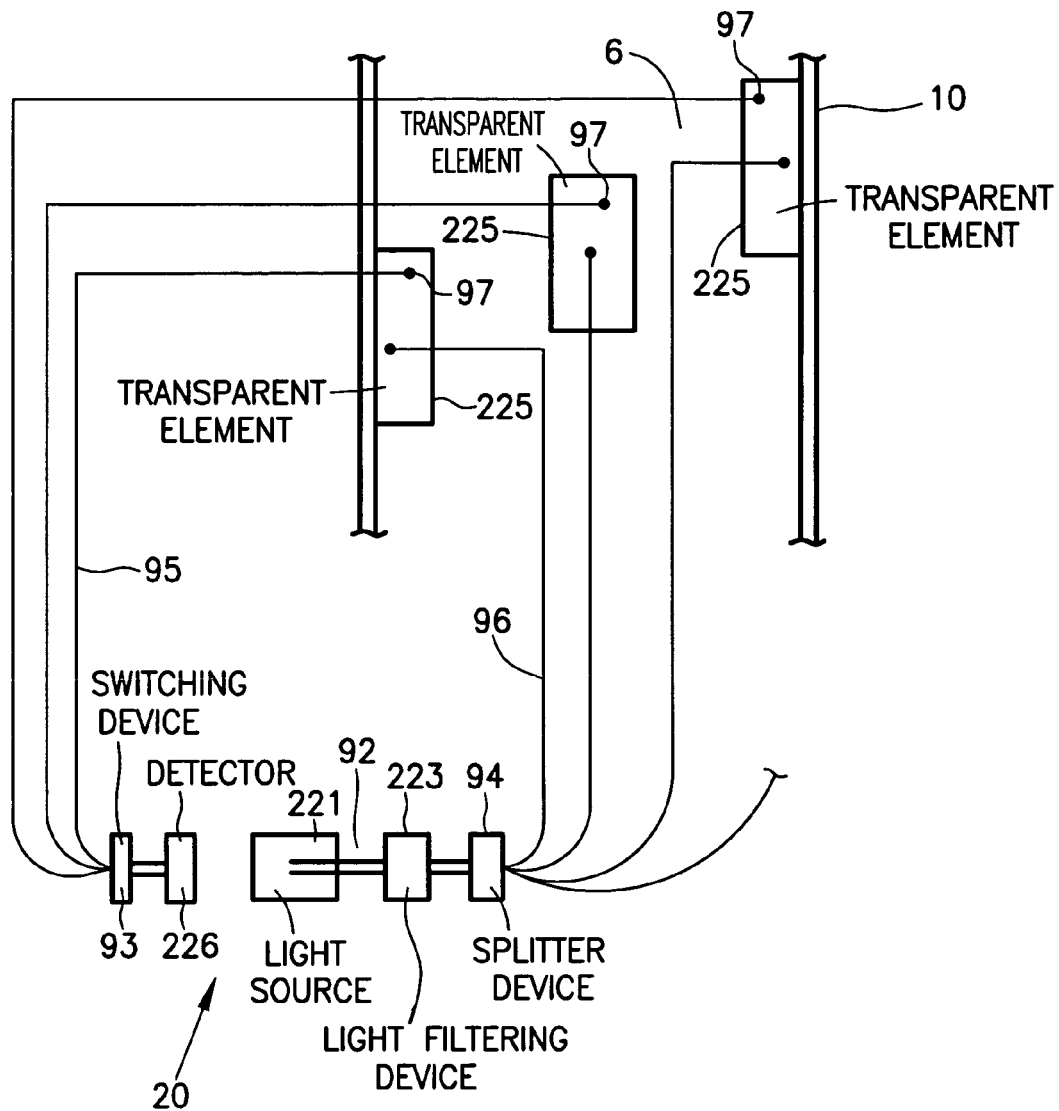
FIG. 5 shows a schematic representation of an embodiment of the present invention wherein in a single detector is interfaced to multiple fiber optic light guides.

FIG. 5 shows an embodiment of the invention having a single spectrometer 21 with a plurality of transparent elements 225 disposed as different longitudinal levels about the circumference of blender 10. This embodiment, like the embodiment shown in FIG. 4, may be especially useful for analyzing for stratification in product 11. In this embodiment, like that shown in FIG. 4 and discussed above, light source 221 including fiber optic bundle 92 is provided. Fiber optic bundle 92 is optically connected to filtering, or monochromator, device 223. Filtering device 223 may be a grating, interferometer, filter wheel, or other suitable device for producing a monochromatic beam of light in each fiber of fiber optic bundle 92. Splitter device 94 is provided for splitting fiber optic bundle 92 into plurality of individual fibers 96, which illuminate respective multiple positions, or angles, in blender 10 via respective transparent elements 225. In applications in which the blender housing rotates (such as in a V-blender), components 221, 92, 23, 93, 36, and 94 are preferably secured to the rotating blender housing (e.g. container 19 of FIG. 1 in the case of a V-blender)

In the embodiment shown in FIG. 5, single detector 226 is provided. Detector 226 may be a photo diode relay or a single element detector combined with a monochromator interferometer, for example. Switching device 93 interfaces detector 226 with fiber optic light guides 95, each connected to a respective sampling position 97 at a respective transparent element 225. Each fiber optic light guide 95 receives diffusively reflected or transmitted, etc., light from product 11. Switching device 93 selects one sampling position 97 at a time and presents the received light to detector 226. This embodiment may be used to read out each sampling position 97 in a desired sequence in a relatively short period of time. Any desired number of sampling positions 97 may be provided situated in any desired configuration about blender 10. In other embodiments of the present invention (not shown) respective individual light sources 221 may be provided for each transparent element 225, instead of using splitter device 94 plurality of individual fibers 96.

As stated above, the digital signal can be transmitted from transmitter 230 to receiver 231 by any known technique in the wireless transmission art, such as transmission using carrier waves in the IR, radio, optical or microwave region of the wavelength spectrum. Infrared (IR) transmission uses an invisible portion of the spectrum slightly below the visible range. The IR transmission can be directed, which requires a direct line-of-site, or diffuse, which does not require line of sight.

Radio transmission uses the radio region on the spectrum, which is located above the visible portion of the spectrum. Suitable devices that allow digital signals to be transmitted in the FM radio region of the spectrum are made by Aeolus and Xircon. In certain embodiments, Xircon's Core Engine can be directly embedded in the electronics of transmitter 230 and receiver 231. In certain embodiments, transmitter 230 and receiver 231 can be linked to a Wi-Fi certified wireless network anywhere in the world, and GSM/CDMA, LAN and WAN connections can also be provided, using devices provided, for example, by 3Com or Nokia.

The digital signal may also be wirelessly transmitted from transmitter 230 to receiver 231 in the microwave frequencies, which are located below the visible range of the spectrum. Nokia microwave radios, for example, can provide a microwave link between transmitter 230 and receiver 231.

Optical devices, such as those based on lasers, can also be used to transmit the digital signal from transmitter 230 to receiver 231.

Once receiver 231 receives the digital signal from transmitter 230, receiver 231, in turn, transmits the digital signal to a processing device 232 to which it is coupled, by any known method. Processing device 232 can be physically coupled to receiver 231, as illustrated in FIG. 2A such as through conventional cables, wires or data buses, in which case such transmission takes place through such physical connections. Processing device 232 can also be separate from receiver 231 and coupled thereto wirelessly, in which case such transmission from receiver 231 to processing device 232 takes place through any of the wireless methods discussed above. Upon receipt of the digital signal from receiver 231, processing device 232 can then process the digital signal as well as transmit the digital signal to peripherals, such as a display device 233 and/or storage device 234. In a network embodiment, processing device 232 can transmit the digital signal to subsequent processing devices. In the embodiment shown in FIG. 2G, for example, processing device 232 can transmit the signal to a further remote device 238, which can transmit the digital signal to peripherals, such as a display device 233 and/or storage device 234.

The communication between spectrometer 21, receiver 231 and the processing device 232 in FIGS. 1–2F (as well as with remote device 238 in FIG. 2F) can also be via a wireless peer-to-peer network. In such a network, spectrometer 21 and attached transmitter 230 send the digital signal to processing device 232 and receiver 231, which can, for example, be a laptop PC equipped with wireless adapter card, via a wireless connection. From processing device 232, a user can analyze the digital signal, transform the digital signal, compare the digital signal to the data set in storage device 234 or display the digital signal on display device 233. Processing device 232 can be moved, so that communication with other spectrometers is possible without the need for extensive reconfiguration. In this embodiment, spectrometer 21 and transmitter 230 function as a client, while processing device 232 acts as a server.

A data reduction technique, such as a partial least squares, a principal component regression, a neural net, a classical least squares (often abbreviated CLS, and sometimes called The K-matrix Algorithm), or a multiple linear regression analysis can then be used to generate a modeling equation from the digital signal.

In certain embodiments, processing device 232 can use various algorithms to pre-treat the spectral data prior to modeling the data via the data reduction technique. For example, a baseline correction, a normalization of the spectral data, a first derivative on the spectral data, a second derivative on the spectral data, a multiplicative scatter correction on the spectral data, a smoothing transform on the spectral data, a Savitsky-Golay first derivative, a Savitsky-Golay second derivative, a mean-centering, Kubelka-Munk transform, and/or a conversion from reflectance/transmittance to absorbence can be performed. The pre-treated data signal can be displayed to the user as a spectrograph (a graphical representation of absorption as it relates to different wavelengths). One or more of these above-mentioned treatments can be performed on the data in any order desired.

A user nay select which pre-treatments and/or reduction techniques to use in transforming or modeling the data. In certain embodiments, the pre-treatments and/or reduction techniques may also be selected pursuant to a set of rules specifying which algorithms to use for a particular type of composition.

Figure 6:
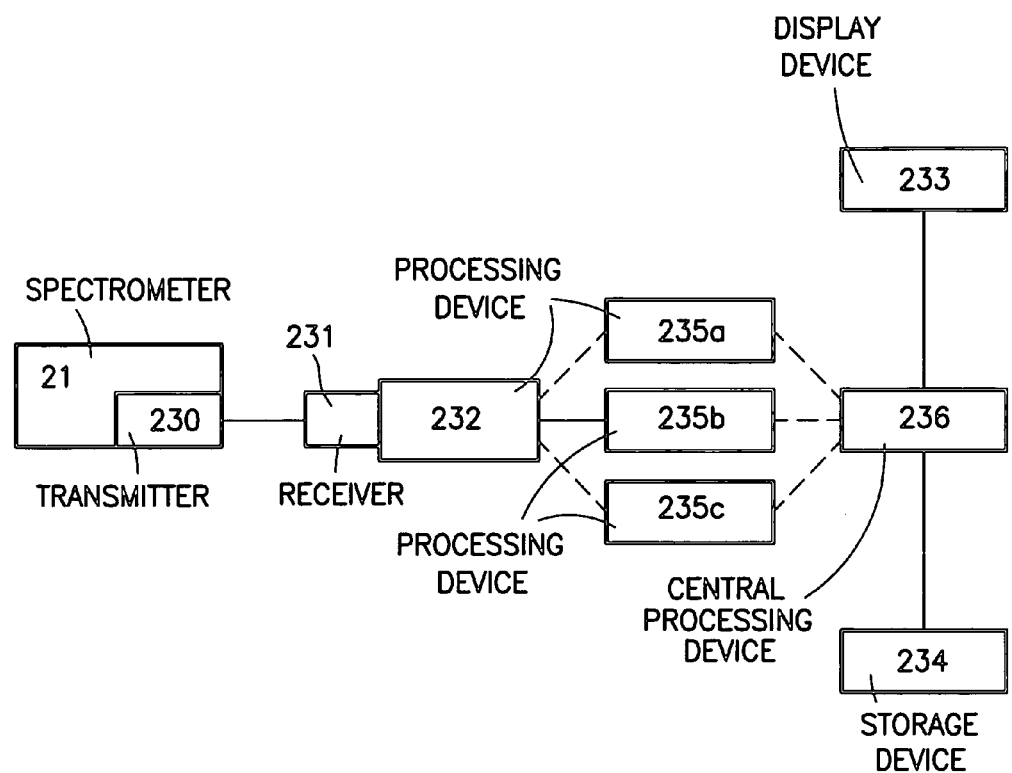
FIG. 6 shows a schematic representation of a configuration for transmitting the digital signal to a processor.

FIG. 6 shows a schematic representation of a configuration for transmitting the digital signal between spectrometer 21 and a central processing device 236, with multiple processing devices 232 and 235a, 235b, 235c arranged in a distributive network. In this configuration, spectrometer 21 includes transmitter 230 and wirelessly transmits a digital signal to receiver 231. The first processing device 232 (e.g., a routing device) receives the digital signal from receiver 231 and transmits a first portion of the digital signal to processing device 235*a* (e.g., a computer in a distributive network), a second portion of the digital signal to processing device 235*b*, and a third portion of the digital signal to processing device 235*c*. Processing devices 235*a*, 235*b*, 235*c* perform various functions on their respective portions of the digital signal in parallel (e.g., transformations of the digital signal) and then each transmits a modified digital signal to a fifth processing device 236 (e.g., a personal computer). Processing device 236 analyzes and transmits the digital signal to display device 233 (e.g., a monitor) and to storage device 234 (e.g., a hard disk). The communication between any of the devices can be via wireless communication, or the devices can be physically connected (e.g., copper wire or fiber optic cable).

Although only one spectrometer 21 with a transmitter 230 is shown in FIG. 6, an arrangement with a plurality of spectrometers, each connected to the same processing unit or distributed over the plurality of processing units, is possible. Similarly, it should be understood that the present invention is not limited to the number or configuration of processing devices 232, 235*a*, 235*b*, 235*c* and 236 shown in FIG. 6. Other configurations, with more or fewer processing devices, are possible.

Figure 7:
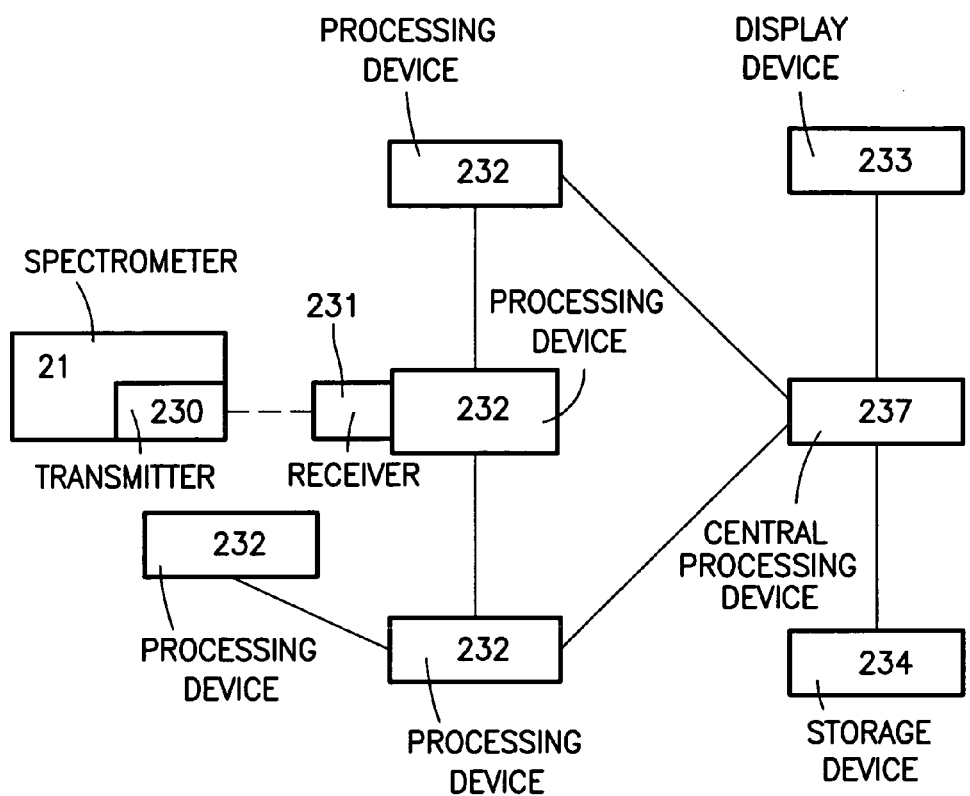
FIG. 7 shows a schematic representation of another configuration for transmitting the digital signal to a processor.

FIG. 7 shows a schematic representation of another configuration for transmitting the digital signal to a processor, between a plurality of processing devices 232 and a central processing device 237. Spectrometer 21 with associated transmitter 230 wirelessly transmits the digital signal to a receiver 231, which is integrated within or coupled to one of processing devices 232 and in connection therewith. Each processing device 232 (e.g., a routing device) transmits the digital signal either to central processing device 237 or to a different processing device 232. Central processing device 237 analyzes the digital signal. Central processing device 237 processes the digital signal and may also transmit the digital signal or selected portions of the data contained therein to display device 233 (e.g., a monitor) where it is displayed in human readable form. Central processing device 237 may also transmit the digital signal or selected portions therein to storage device 234 (e.g., a hard disk). The communication between any of the devices can be via wireless communication (e.g., radio waves). The devices can also be physically connected (e.g., by wire or fiber optic cable). Furthermore, central processing unit 237 can be mobile, such as by being mounted in a mobile platform (e.g., a laptop or hand-held device) or by itself having a mobile structure, such as a lap-top computer, so that central processing unit 237 can be placed at different positions with respect to the network. Although only one spectrometer 21 with a transmitter 230 is shown in FIG. 5, an arrangement with a plurality of spectrometers 21, each connected to the same processing unit or distributed over the plurality of processing units 232, is possible.

In certain embodiments, transmitter 230 can be a transmitter/receiver device, so that the spectrometer 21 may function with a Global Positioning System (GPS). GPS technology allows tracking of the device and may prove helpful if the spectrometer is lost or stolen. Furthermore, the GPS coordinates of blender 10 can be sent, along with the digital signal, to a central database, so that, if a problem is detected regarding blender 10, a repair technician could be sent directly to the hopper by using the hopper's GPS coordinates. Thus, a manufacturing plant that continues to have problems could more easily be ascertained.

Figure 8:
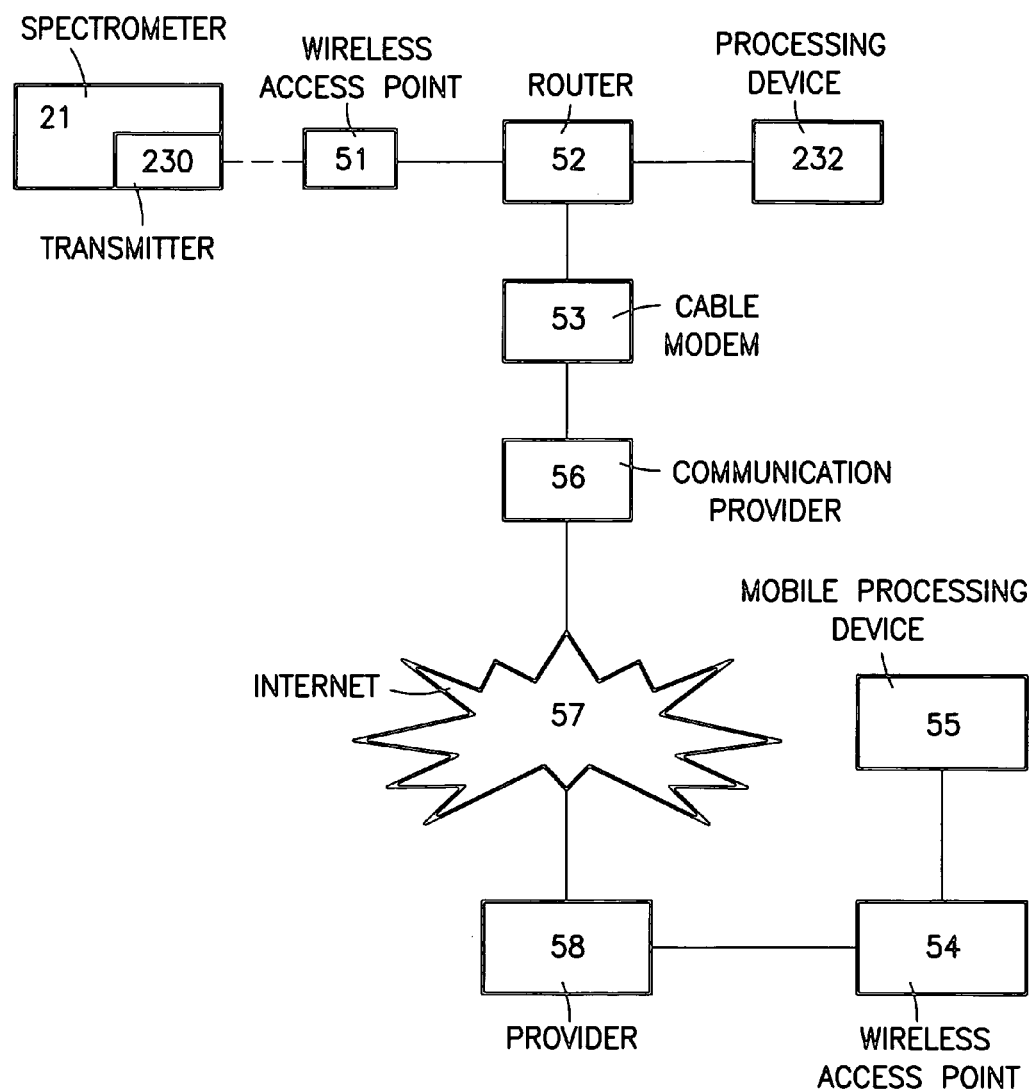
FIG. 8 shows a schematic representation of a networking arrangement for transmitting the digital signal in accordance with another embodiment of the present invention.

FIG. 8 shows a schematic representation of a networking arrangement for transmitting the digital signal in accordance with another embodiment of the present invention. The wireless access point 51 can be any suitable device, such as Linksys's WAP11. Spectrometer 21 wirelessly transmits the digital signal to wireless access point 51 by transmitter 230. Wireless access point 51 then transmits the digital signal to a router 52 via a physical connection. Router 52 can be any suitable device, such as a Linksys' BEFSR41 4-port cable/DSL router. Router 52, in turn, transmits the data to processing device 232 and a cable modem 53. Router 52 can be connected to processing device 232 and cable modem 53 by any suitable device, such as, for example, a 10BaseT connector. At processing device 232, a user may perform functions on the data, view the data and/or store the data. Cable modem 53 transmits the digital signal over existing phone lines to a communication provider 56, e.g., AT&T, which in turn uses existing networks to transfer the digital signal to the Internet 57. From the Internet 57, the digital signal is received by another communication provider 58, e.g., America Online, which transmits the digital signal to a second wireless access point 54. Second wireless access point 54 can be any suitable device, such as a Linksys' WAP11. Provider 58 can be connected to second wireless access 54 point by, for example, existing phone lines. Second wireless access point 54 transmits the digital signal to a mobile processing device 55, such as a laptop computer, equipped with a wireless card. The wireless card can be any suitable device, such as, for example, 3Com's Wireless AirConnect PC card. From mobile processing device 55 with the wireless card or the processing device 52, a user can perform functions on the digital signal, the digital signal can be displayed and/or the digital signal can be stored.

Figure 9:
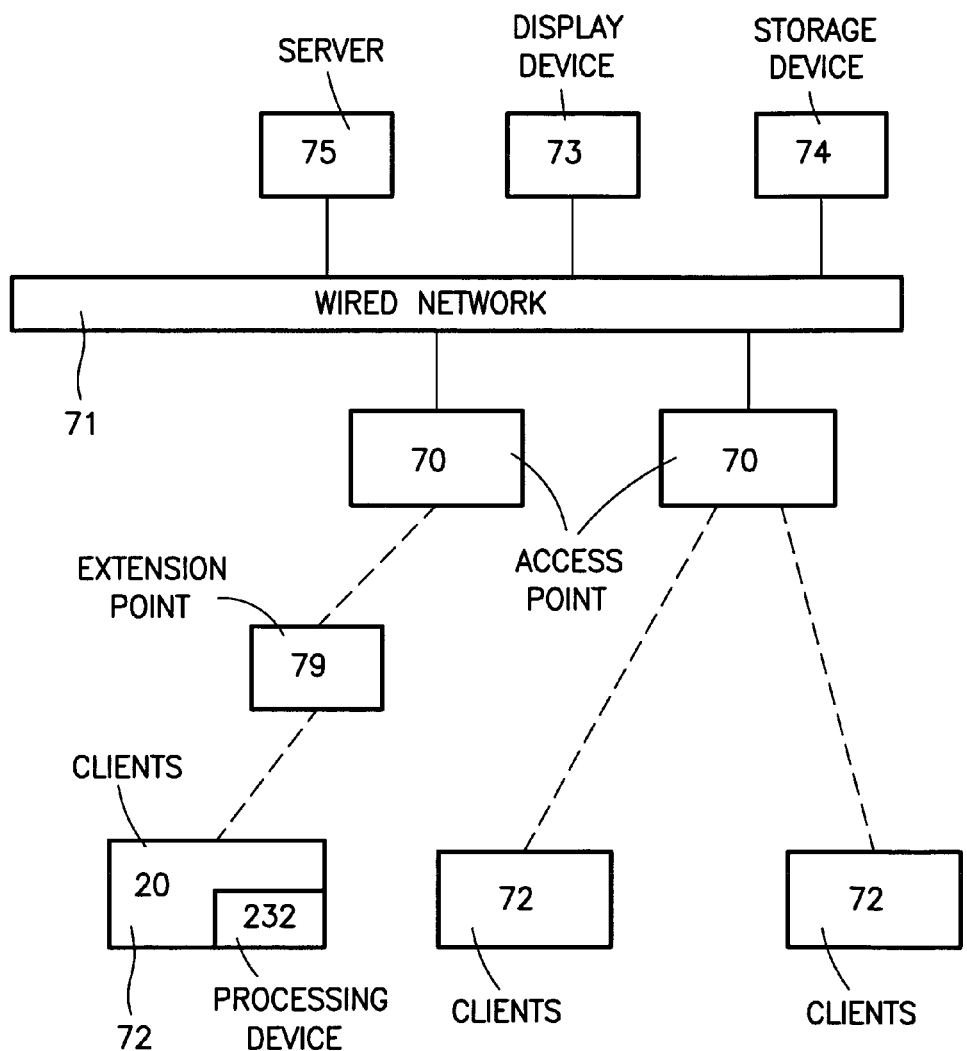
FIG. 9 shows a schematic representation of another embodiment of a networking arrangement for transmitting the digital signal.

FIG. 9 illustrates a plurality of clients 72 and a plurality of access points 70 arranged in a wireless network. In this embodiment, spectrometer 21 and transmitter 230 function as one of the clients 72. Clients 72 can also be processing device 232 (e.g., a PC or a lap-top). Each client 72 can wirelessly transmit the digital signals to a wired network 71 by transmitting to one of access points 70. Access points 70 extend the range of the wired network 71, effectively doubling the range at which the devices can communicate. Each access point 70 can accommodate one or more clients 72, the specific number of which depends upon the number and nature of the transmissions involved. For example, a single access point 70 can be configured to provide service to fifteen to fifty clients 72. In certain embodiments, clients 72 may move seamlessly (i.e., roam) among a cluster of access points 70. In such an embodiment, access points 70 may hand client 72 off from one to another in a way that is invisible to the client 72, thereby ensuring unbroken connectivity.

Once the digital signal enters wired network 71, the digital signal call be relayed to a server 75, the display device 73 and the storage device 74, as well as to other clients 72. Server 75 or other clients 72 can convert the digital signal to a spectrograph and/or perform various algorithms on the digital signal.

In certain embodiments, an extension point 79 is provided. Extension points 79 augmented the network of access points 70 and function like access points 70. However, extension points 79 are not tethered to wired network 71 as are access points 70. Instead extension points 79 communicate with one-another wirelessly, thereby extending the range of network 71 by relaying signals from a client 72 to an access point 70 or another extension point 79. Extension points 79 may be strung together in order to pass along messaging from an access point 70 to far-flung clients 72.

Figure 10:
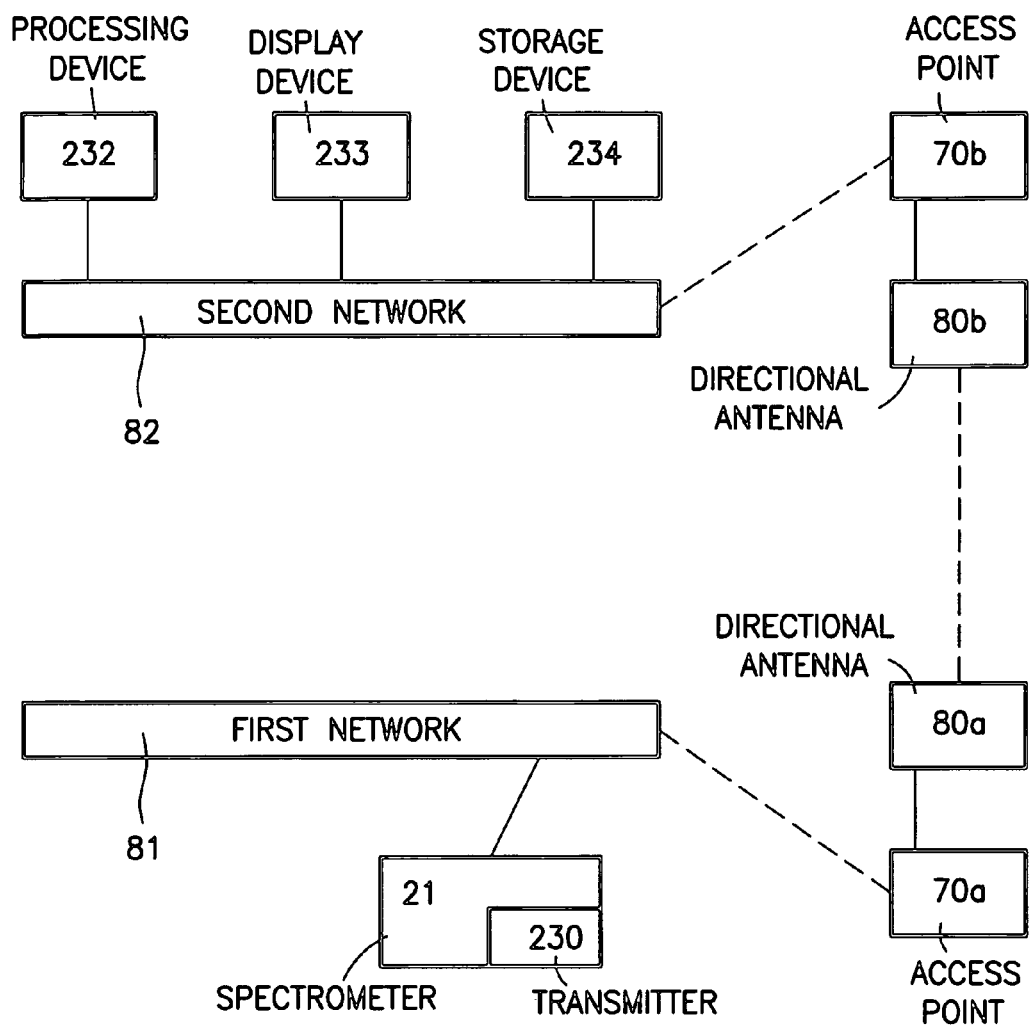
FIG. 10 shows a schematic representation of a networking arrangement for transmitting the digital signal in accordance with yet another embodiment of the present invention.

FIG. 10 shows a schematic representation of a networking arrangement for transmitting the digital signal in accordance with yet another embodiment of the present invention. Communication between first and second networks 81,82 is by directional antennas 80a,80b. Each antenna 80a,80b targets the other to allow communication between networks 81,82. First antenna 80a is connected to first network 81 via an access point 70a. Likewise, the second antenna 80b is connected to second network 82 by an access point 70b. The digital signal from spectrometer 21 is transmitted by transmitter 230 to first network 81 and is then transmitted to the directional antenna 80a by being relayed over the nodes of first network 81. The digital signal can then be transmitted to second directional antenna 80b on second network 82. Second network 82 then relays the digital signal to processing device 232, display device 233 and/or the storage device 234.

Figure 11:
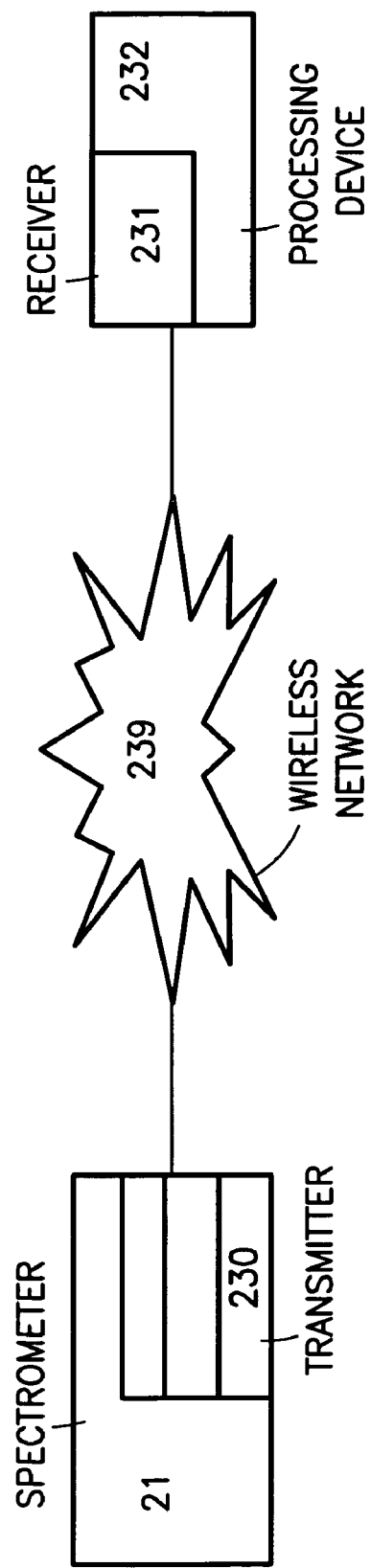
FIG. 11 shows a schematic representation of still another networking arrangement for transmitting the digital signal.
Figure 12:
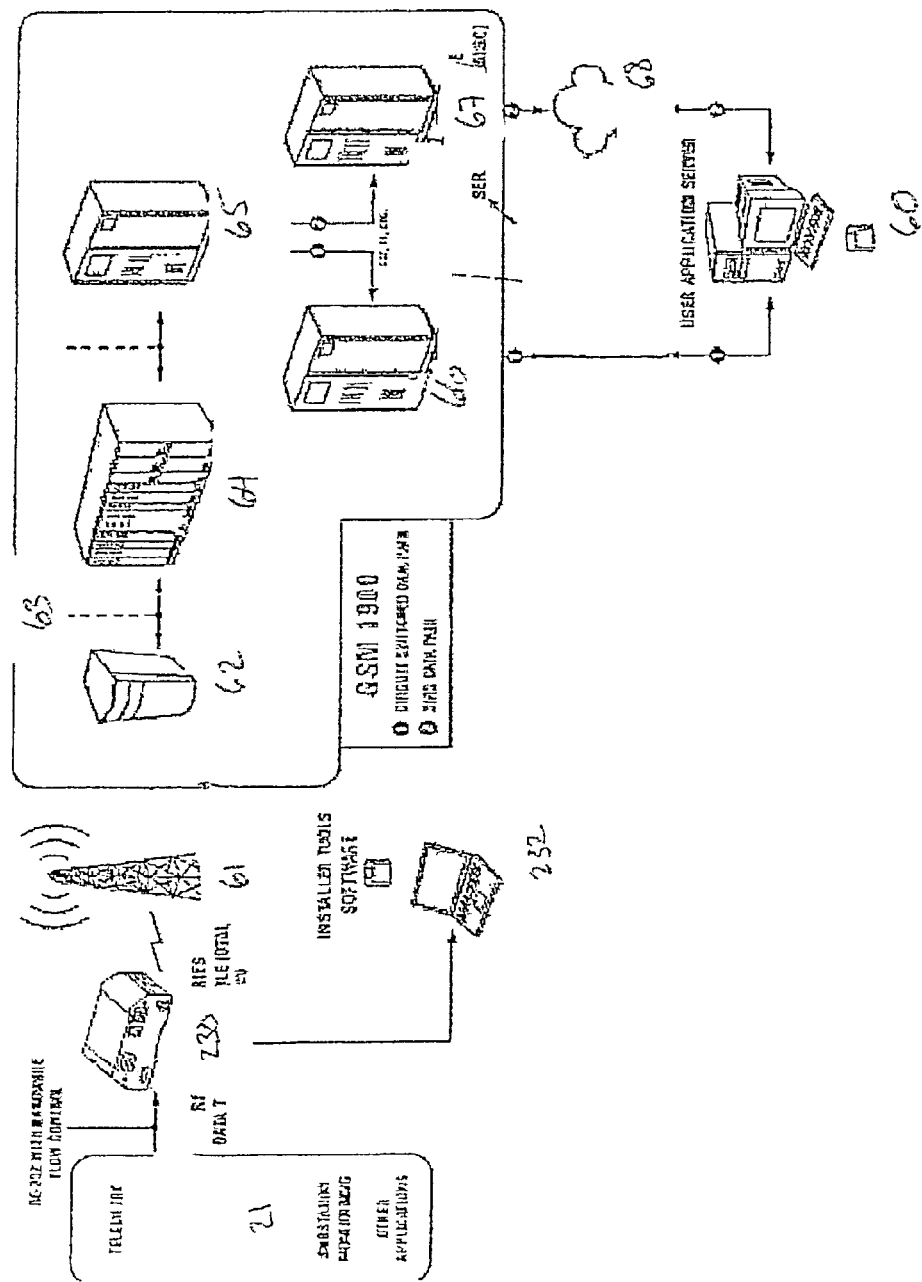
FIG. 12 shows a schematic representation of a further networking arrangement for transmitting the digital signal.

FIG. 11 shows the communication between spectrometer 21 and processing unit 232 via an existing wireless network 239. The data from spectrometer 21 is fed into a transmitter 230 located in or attached to spectrometer 21. Transmitter 230 can be, for example, the type of transmission device used in a conventional cell phone. Transmitter 230 then collects to the processing device 232 equipped with a receiver 231 (e.g., a receiver used in current cell phone technology) by opening a communication channel specific to the processing device 232 oil wireless network 239 (e.g., dialing a cell phone number). Once the communication channel is established, the digital signal is then transferred to processing device 232 by routing the digital signal through the existing wireless network 239. Processing device 232 can then be connected to another network or a display device and/or storage device. Wireless network 239 can be any suitable network, such as, for example, SkyTel or Nokia's communication network. In certain embodiments, wireless network 239 can be included as part of a wireless LAN, wireless WAN, cellular/PCS network (e.g., by using a transceiver equipped with a CPDP modem), digital phone network, proprietary packet switched data network, One-way Pager, a Two-way Pager, satellite, Wireless local loop, Local Multi-point Distribution Service, Personal Area Network, and/or flee space optical networks, FIG. 12 shows the communication between the spectrometer 21 and an application server 60 via a wireless network. Spectrometer 21 sends the digital signal to transmitter 230, which can be, for example, Xircon's Redhawk II™. Transmitter 230 then wirelessly sends the digital signal to processing device 232, which can be, for example, a laptop computer, and to a long range transmission device 61, which transmits the digital signal to a base transceiver station 62 via a modulated radio wave. Then, through a T1 line 63, the digital signal is transmitted to a base station controller 64, which in turn transmits the digital signal to a mobile switching center 65. Based on a pre-defined user setting, mobile switching center 65 transmits the digital signal to either an interworking function device 66 or a short message center 67. If the digital signal is sent to interworking function device 66, interworking function device 66 then transmits the digital signal to an application server 60. However, if the digital signal is sent to short message center 67, short message center 67 routes the digital signal over the Internet 68 and on to the application server 60. Application server 60 provides for display of the digital signal, transfer of the digital signal to a client of server 60, analysis of the digital signal, and/or storage of the digital signal. Application server 60 can be any suitable device, such as, for example, an IBM compatible Gateway PC.

It should be apparent that the FIGS. 1–12 show merely exemplary embodiments, and other embodiments will be apparent to one skilled in the art.

Figure 13A:
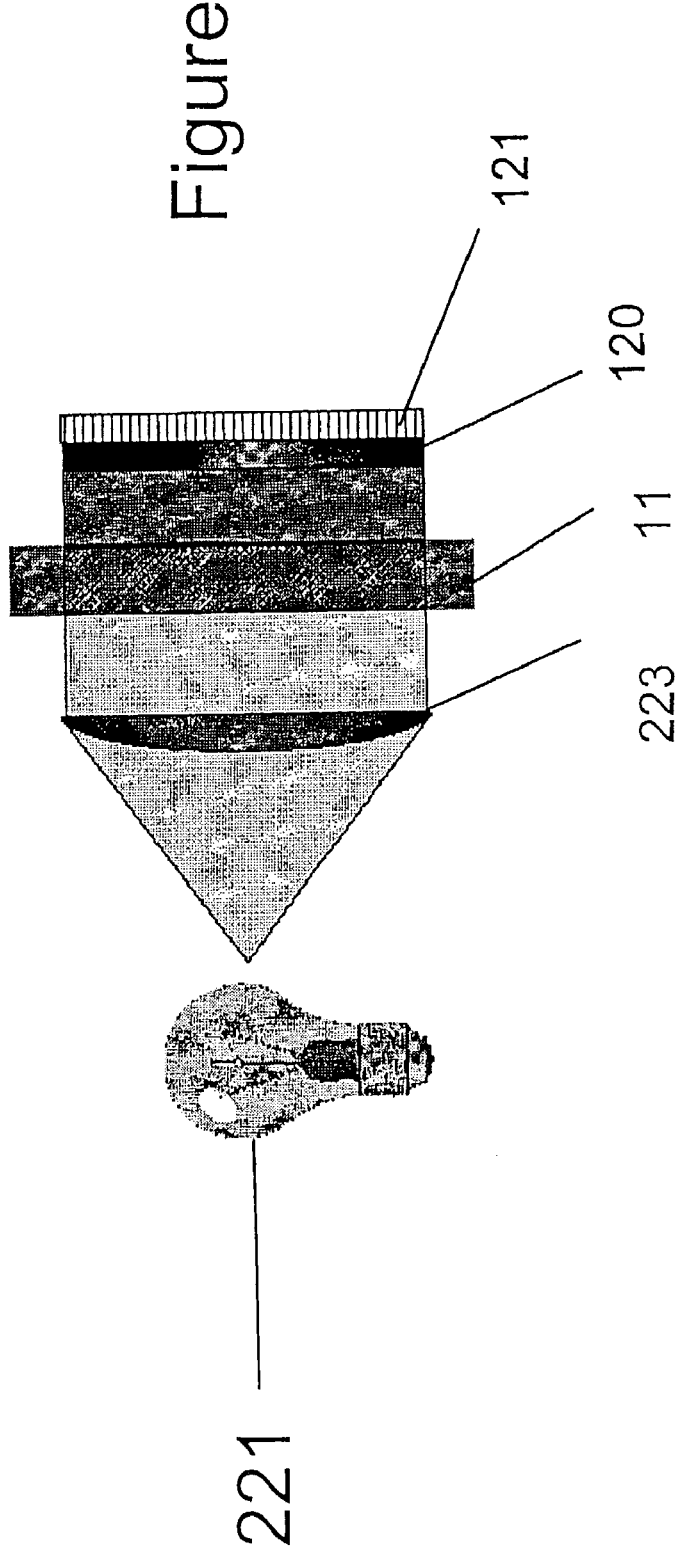
FIGS. 13A–B show an illustrative remote spectrometer for performing spectral scans.
Figure 13B:
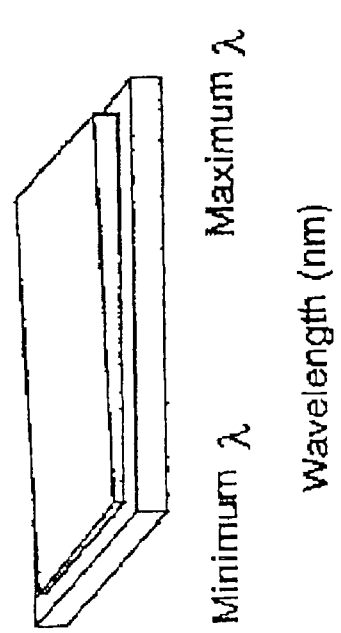

FIGS. 13A–B show an illustrative remote spectrometer for performing spectral scans. As illustrated in FIG. 13A, a multiple wavelength photometer has light source 221 that produces a light beam that is focused and directed onto product 11 by focusing optics 225. The light that is transmitted through product 11 is passed through a linear variable filter 120 to an array detector 121 in order to filter and receive a number of specific, predetermined narrow bands of wavelengths simultaneously. Linear variable filters are well known in the art and are described in, for example; U.S. Pat. No. 6,057,925 to Anthon, U.S. Pat. No. 5,166,755 to Gat and U.S. Pat. No. 5,218,473 to Seddon et al., and are shown schematically in FIG. 13B. Focusing optics 225 can form a portion of wall 14 of blender container 19. In other embodiments, focusing optics 225 can be located outside container 19, in which case the light beam passes through window 12 in container 19 after impinging on focusing optics 225. Likewise, linear variable filter 120 and array detector 121 may form a portion of wall 14 of container 19. In other embodiments, linear variable filter 120 and array detector 121 can be located outside container 19, in which case the light beam passes through a second window in container 19 and then impinges on linear variable filter 120. Most preferably, linear variable filter 120 and array detector 121 may be used and positioned very much in the same way as focusing optics 225 and detector 226 are used and positioned in the embodiments and versions discussed elsewhere herein, such as those shown in FIGS. 2A–G and FIG. 3.

Figure 14A:
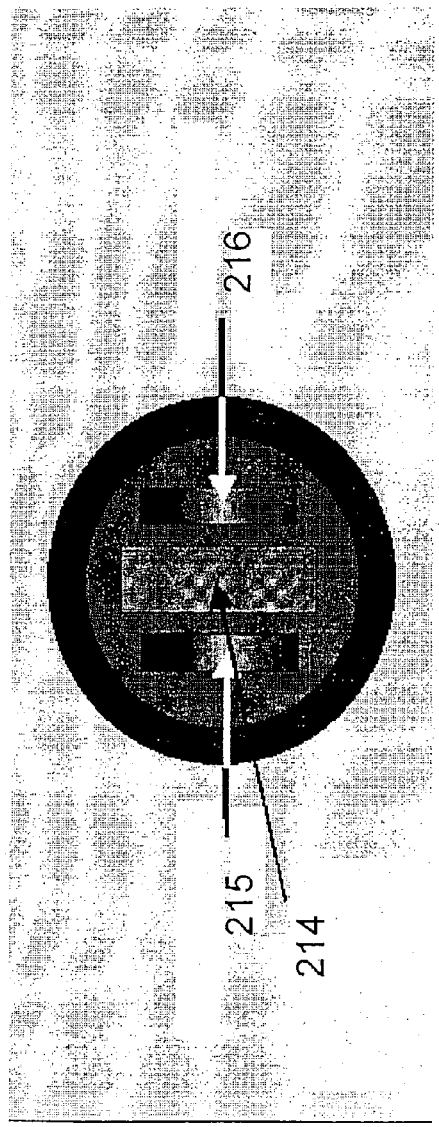
FIGS. 14A–B illustrate spectroscopic detector arrangements.
Figure 14B:
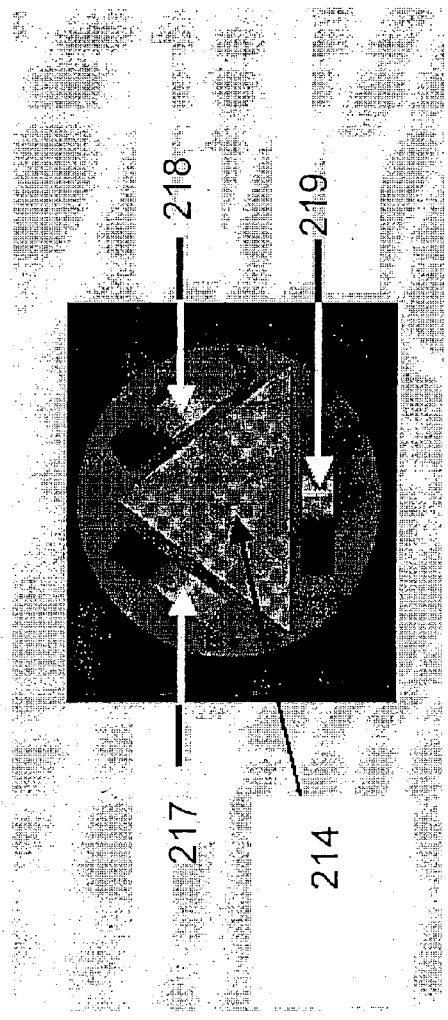

FIGS. 14A and 14B illustrate spectroscopic detector arrangements. As shown in FIG. 14A, the device includes a light emitting portion 214 and two detectors 215, 216 that surround light emitting portion 214 and can be embedded in the wall of container 19. Light emitting portion 214 has a light source that could be any light source, such as a quartz halogen lamp with integrated focusing optics or a fiber optic bundle, and light emitting portion 214 preferably has a rectangular prism $SiO_2$ light guide. At predetermined intervals, light emitting portion 214 emits light onto product 11. Detectors 215,216 then detect the light reflected off product 11. Detectors 215,216 are preferably formed of silicon and are preferably designed to detect only a specific range of wavelengths. For example, detector 215 could be set to detect light at wavelengths of only 400–700 nm, and detector 216 could be set to detect light at wavelengths of only 600–1100 nm. As such, the device shown in FIG. 13A would be able to detect light wavelengths of 400–1100 nm.

In one embodiment, detectors 215,216 can detect light at their specific wavelength ranges due to the presence above each filter 215,216 of an optical filter that restricts the transmission of light to detectors 215,216 at wavelengths in only the respective specified ranges.

In another embodiment, detectors 215,216 are array detectors and can detect light at their specific wavelength ranges due to the presence above each detector 215,216 of a linear variable filter 120, as shown in FIGS. 13A–B, that restricts the transmission of light to detectors 215,216 at wavelengths in only the specified, predetermined narrow band of wavelengths.

In a further preferred embodiment of a remote spectrometer, as shown in FIG. 14B, the device includes a light emitting portion 214 and three detectors 217,218,219, that surrounding light emitting portion 214. Light emitting portion 214 has a light source that could be any light source but is preferably a quartz halogen lamp with integrated focusing optics, and light emitting portion 214 preferably has a triangular prism SiO$_2$ light guide. At predetermined intervals light emitting portion 214 emits light onto granulation 6. Detectors 217–219 then detect the light reflected off granulation 6. The spectrometer of FIG. 14B is similar to the spectrometer of FIG. 14A, except that light emitting portion 214 is located among three detectors, rather than two detectors in FIG. 14A.

Detectors 217–219 are designed to detect only specific bands of wavelengths. For example, detectors 217–219 are preferably formed of silicon, with detector 217 detecting light at wavelengths of 400–700 nm, and detector 218 detecting light at wavelengths of 600–1100 nm. In addition, detector 219 is preferably formed of indium/gallium/arsenic (InGaAs) and detects light at wavelengths of 11–1900 nm. As such, the device can detect light wavelengths of 400–1900 nm. In one embodiment, detectors 217–219 can detect light at their specific wavelength ranges due to the presence above each detector 217–219 of an optical filter that restricts the transmission of light to detectors 217–219 at wavelengths in only the specified ranges. In another embodiment, detectors 217–219 are away detectors and can detect light at their specific wavelength ranges due to the presence above each detector 217–219 of a linear variable filter 120, as shown in FIGS. 13A–B, that restricts the transmission of light to detectors 217–219 at wavelengths in only the specified, predetermined narrow band of wavelengths.

Most preferably, the embodiments of FIGS. 14A–B may be used and positioned very much in the same way as filter 223 and detector 226 are used and positioned in the embodiments and versions discussed elsewhere herein, such as those shown in FIGS. 2A–2G and FIGS. 2 and 3.

Figure 15:
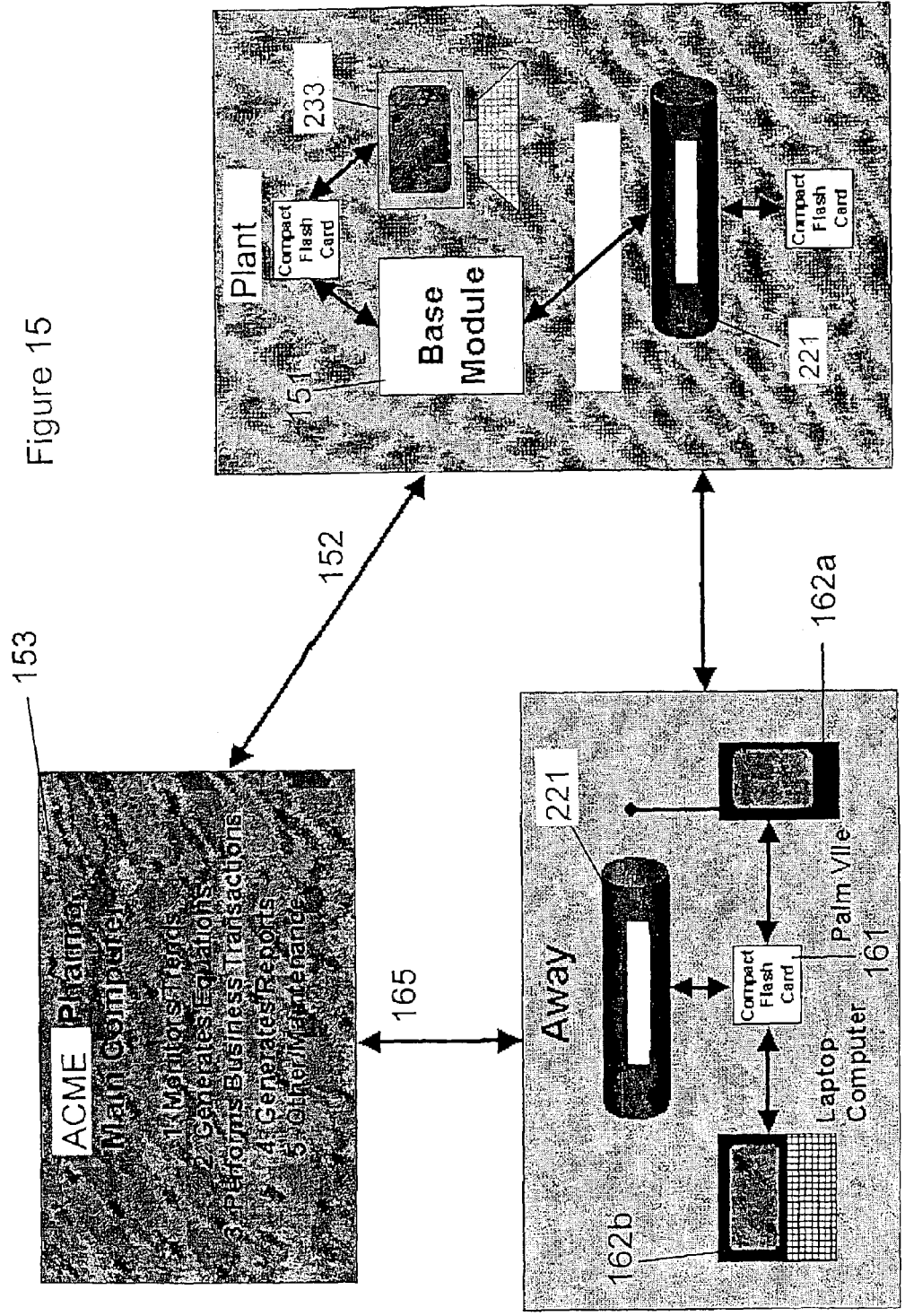
FIG. 15 illustrates the manner in which a remote wireless spectrometer can interact with a central computer.

FIG. 15 illustrates the manner in which a remote wireless spectrometer can interact with a central computer. The present invention, which can be made in accordance with any of the possible embodiments described above, is generally considered to be situated at a pharmaceutical manufacturing plant. The spectrometer 21 is connected, either directly or wirelessly, to a base module 151 that could also be situated at the pharmaceutical manufacturing plant.

In certain preferred embodiments, a further remote communication link 152 is provided between home base computer 151 and a central or main computer 153. This link 152 could be by wireless satellite cable, LAN, telephone link or any other suitable wireless connection, and could be directly from home base computer 151 to main computer 153. Main computer 153 receives and stores the spectral scan from the present invention. Main computer 153 may also monitor the purity of the granulation, including moisture changes in the granulation's profile as well as trends therein, performs analysis thereof, generates and regenerates the a modeling equation for each sample as necessary, generates reports, and performs business transactions and other tasks.

Figure 16:
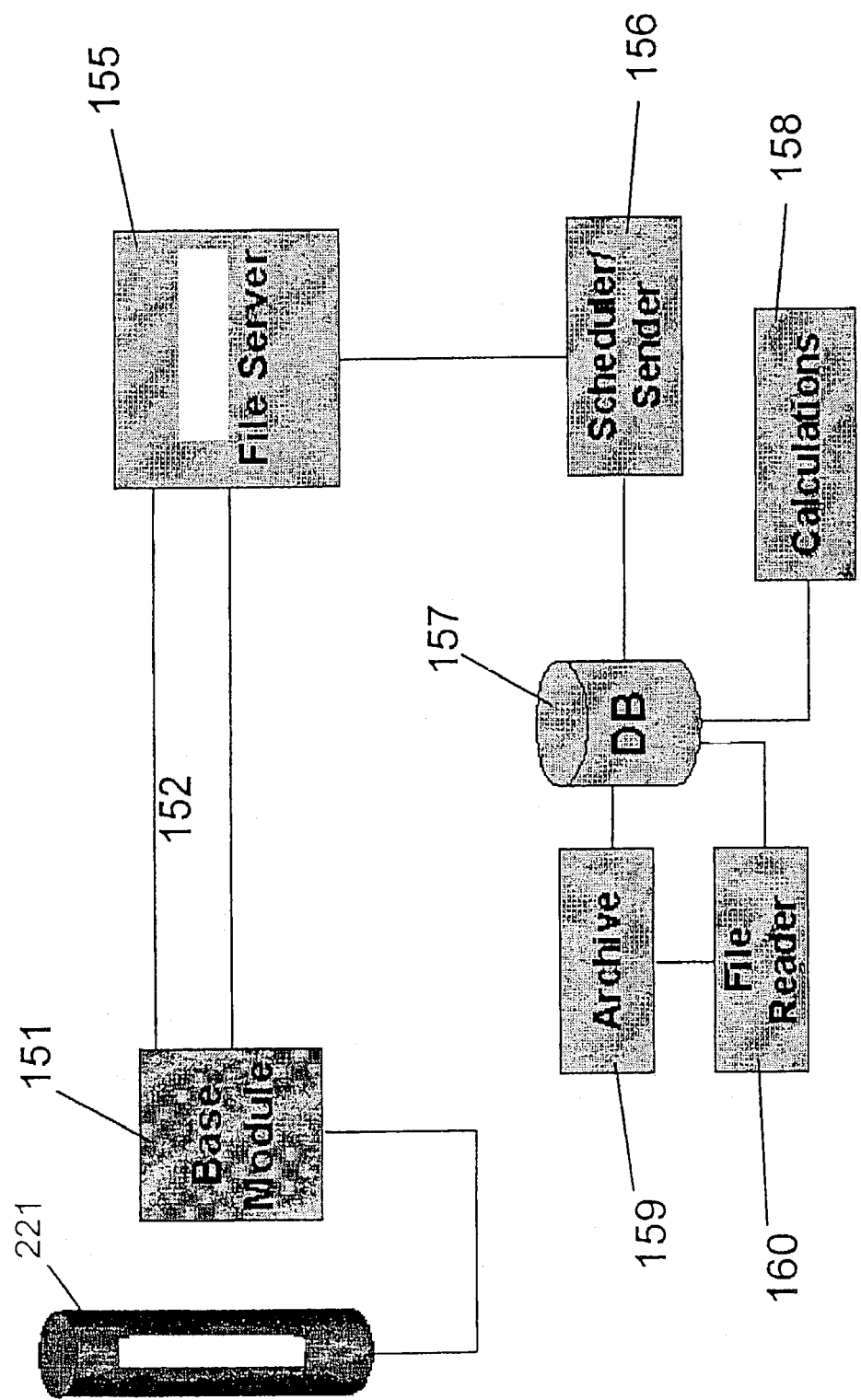
FIG. 16 illustrates in more particular detail the elements of a base connection to the main computer.

FIG. 16 shows in more particular detail the elements of a base connection to the main computer. Spectrometer 21 is connected, either directly or wirelessly, such as via a RS-232 Blue Tooth® Wireless link, to a base module 151. The remote communication link 152 between home base computer 151 and main computer 153 can be additionally by existing dedicated telephone line, such as by dial-up modem, by wireless communication such as satellite cable, LAN, by internet, such as by cable or DSL, or even through a virtual private network (VPN) or any other suitable wireless connection. Main computer 153 preferably comprises a file server 155 that is linked to a database 157 through a scheduler/sender 156. Database 157 is also linked to calculations 158, archive 159 and file reader 160 modules.

Referring again to FIG. 15, in certain circumstances, spectrometer 21 of the present invention can be detached from blender 10 and transported and attached to another blender 10. Such a device could obtain the spectrographic data from a variety of different locations. Modeling equations and results can be stored in a compact flash card 161 that is attached to spectrometer 21. Spectrometer 21 can be connected, either directly or wirelessly, to a portable base module 162, such as a PALM® device 162a or a laptop computer 162b, that typically comprises a processing unit and a display device. Portable base module 162 could also be wirelessly linked to home base computer 152 for downloading and compilation of data. Portable base module 162 could also be wirelessly linked 165 to main computer 153. As discussed previously, these links 165 could be by wireless satellite cable, LAN, telephone link or any other suitable wireless connection.

Figure 17A:
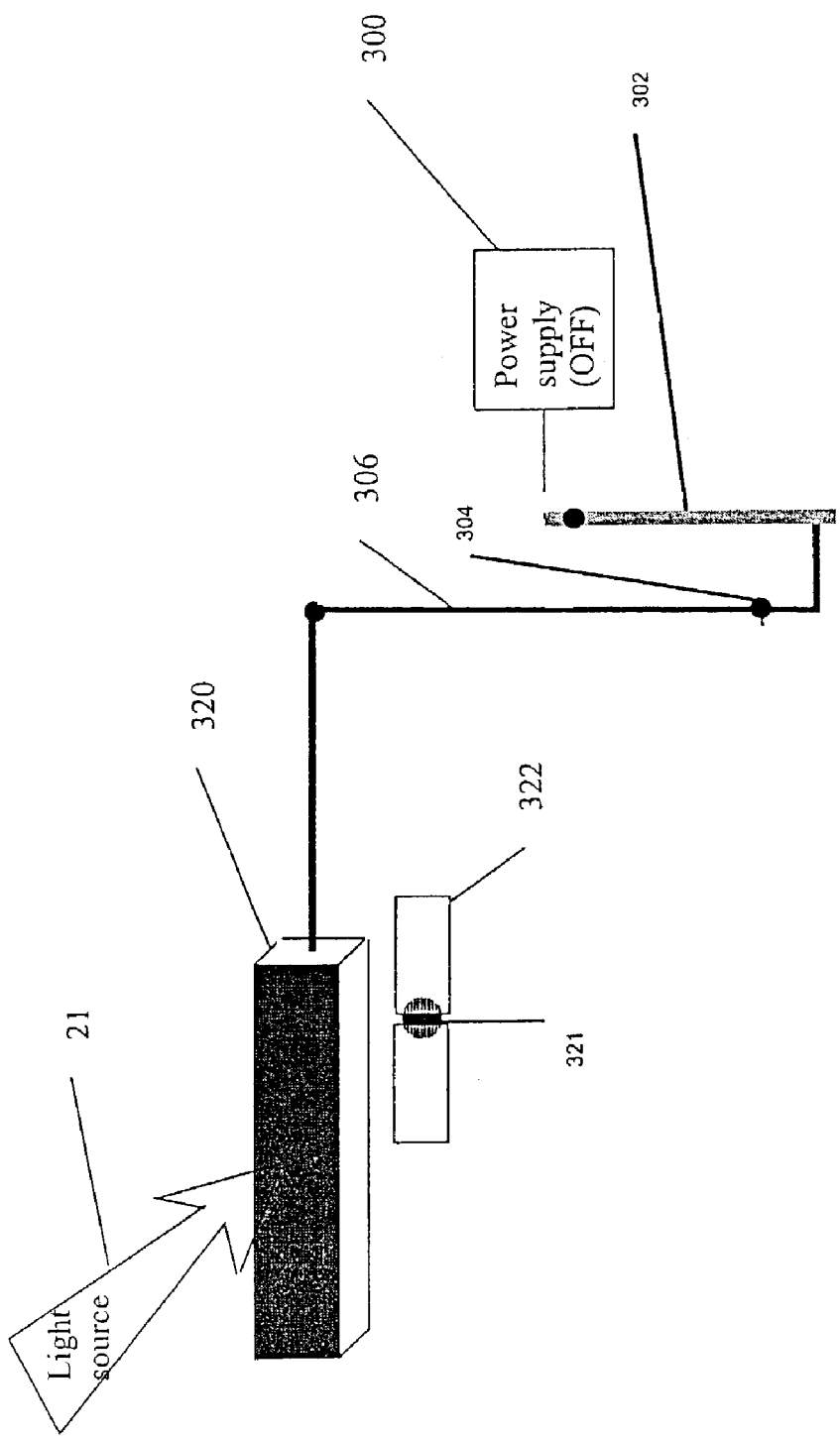
FIGS. 17A–D show a preferred embodiment of a remote spectrometer.
Figure 17B:
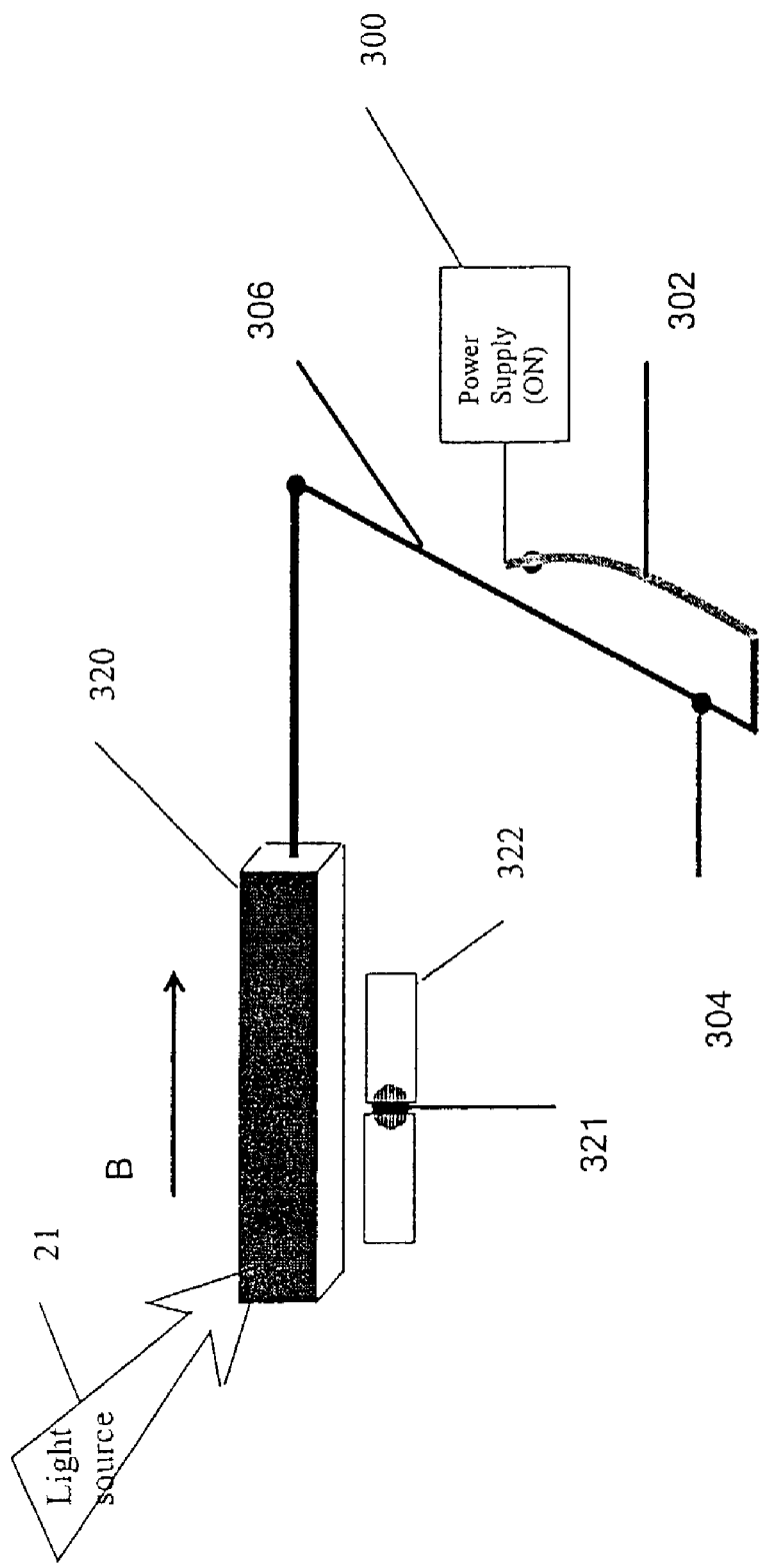

FIGS. 17A–B show another preferred embodiment of a remote spectrometer 21. As illustrated in FIG. 17A, light source 221 produces a light beam that is passed through product 11, through linear variable filter 320, through slit aperture 322 and onto single diode detector 321. As in the embodiment described above with reference to FIGS. 2A–G, the light from light source 221 may pass through near infrared or infrared window/transparent element 23. For example, spectrometer 21 can be set within the window 12, 13 in the wall 14 of container 19. After being transmitted through product (as shown in FIG. 2D), or reflected off of granulation 6 (as shown in FIG. 2F), the light is passed through linear variable filter 320 to, possibly via a detector imaging optic 225 (see FIG. 2A), in order in order to filter the light to a desired bind of wavelengths. The light is then detected by single diode detector 321, either as transmittance or reflectance. In one embodiment, linear variable filter 320 can be arranged as a single range filter, and detector 321 is a single range detector.

The embodiment shown in FIGS. 17A–B is a scanning module because the device is equipped with piezoelectric bimorph (bender) 302 for moving linear variable filter 320 in various directions in order to allow the operator to obtain filtered scans of product 11 at a number of specific, predetermined narrow band of wavelengths in the light. Bimorph 302, powered by power supply 300, is connected to linear variable filter 320 via fulcrum 304 and lever 306, which amplify the displacement of the bimorph. FIG. 17A shows bimorph 302 with power supply 300 off. FIG. 17B shows bimorph 302 with power supply 300 on. With power supply 300 on, bimorph 302 bends as shown in FIG. 18B, forcing the lower portion of lever 306 to pivot about fulcrum 304 in the direction of arrow A. The pivoting of lever 306 causes linear variable filter 320 to move in the direction of arrow B, as indicated. To select each desired wavelength, power supply 300 may be controlled so as to provide predetermined power levels to bimorph 302 and thereby translate linear variable filter 320 to a desired position.

The embodiment of the invention shown in FIGS. 17A–B is "solid state" in the sense that no electric motor is used to move linear variable filter 320. Piezoelectric bimorph 302 may be capable of very precise and repeatable positioning to within fractions of a micron, allowing for advantageous wavelength reproducibility. Linear variable filter 320 may be, for example, 2–3 mm in length, thereby enabling a relatively small overall size of spectrometer 21. Spectrometer 21 may be used in a wavelength range from ultraviolet to the mid infrared (200 nm–10,000 nm) by selecting the appropriate combination of linear variable filter 320 and single diode detector 321.

Figure 17C:
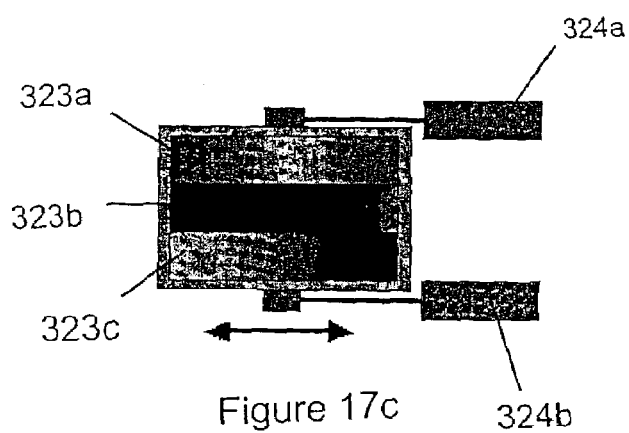
Figure 17D:
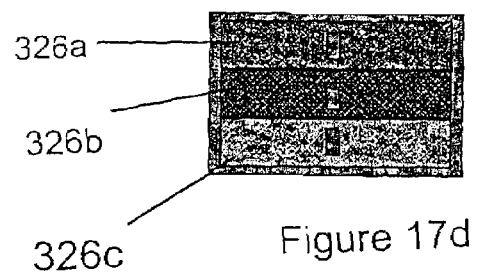

In another embodiment, linear variable filter 323 can be arranged as separate multi-range filters 323a,323b,323c, as shown in top view in FIG. 17C. In this embodiment, each of linear variable filters 323a,323b,323c restricts the transmission of light to wavelengths in only certain specified, predetermined narrow band of wavelengths. For example, linear variable filter 323a transmits light at wavelengths of 400–700 nm, linear variable filter 323b transmits light at wavelengths of 600–1100 nm, and linear variable filter 323c transmits light at wavelengths of 1100–1900 nm. The separate multi-range linear variable filters 323a, 323b, 323c may be moved by respective piezoelectric bimorphs in order to allow the operator to obtain filtered scans of product 11 at a number of specific, predetermined narrow band of wavelengths in the light. When separate multi-range filters 323a, 323b,323c are used, the separate detectors may also be used to detect light at only those specific bands of wavelengths. For example, as shown in top view in FIG. 17D, detectors 326a,326b,326c are situated such that detector 326a detects light at wavelengths of 400–700 nm, detector 326b detects light at wavelengths of 600–1100 nm, and detector 326c detects light at wavelengths of 1100–1900 nm. As such, the device can detect light wavelengths of 400–1900 nm.

The operation of this device will be shown with regard to the multi-range filter and detector embodiment but applies equally to the single range filter and detector embodiment. The operator programs the processing device (not shown) as to the desired wavelengths or ranges of wavelengths to be scanned, and the piezoelectric bimorphs move linear variable filters 323a,323b,323c so as to allow only the desired wavelengths to pass. Thus, the light 21 is filtered to the desired band of wavelengths by linear variable filters 323a, 323b,323c is focused onto array detectors 326a,326b,326c (or one for each of detectors 326a,326b,326c), which detect light at the specific wavelength ranges.

Alternatively, the operator may operate the device manually so as to allow scans to be taken at only the particular wavelengths specified at the time by the operator.

Figure 18:
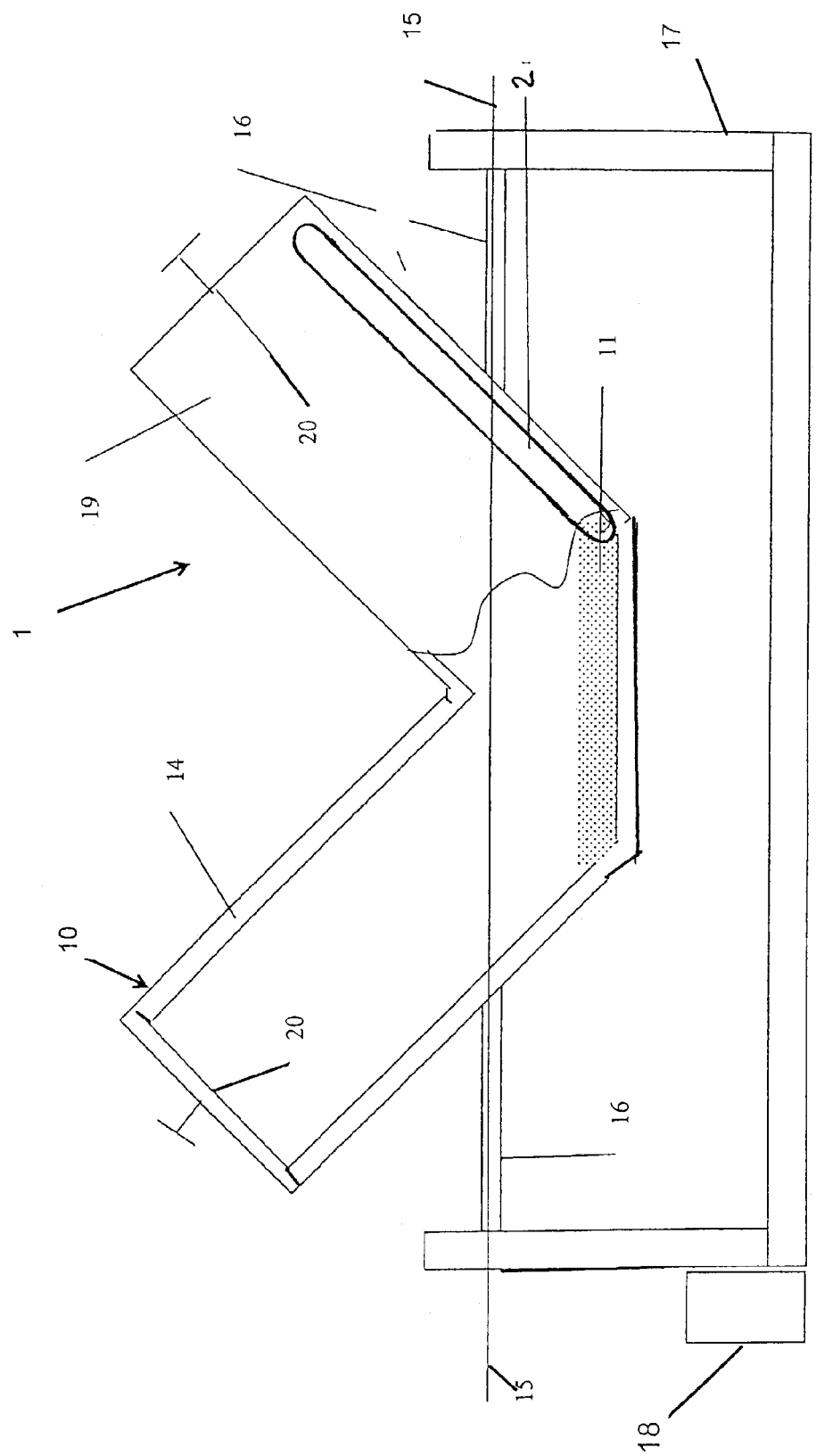
FIG. 18 shows a schematic view of a blending apparatus according to another embodiment of the present invention.

FIG. 18 shows a schematic view of a blending apparatus according to another embodiment of the present invention. In this embodiment container 19 includes elongated window 2 disposed in wall 14. Elongated window 2 may be disposed along a long axis of a leg of "V"-shape container 19, as shown in FIG. 18. Alternatively, in other embodiments elongated window 2 may disposed in any suitable orientation or position of container 19. Additionally more than one elongated window 2, or a combination of elongated and non-elongated windows, may be provided.

A wireless spectrometer (not shown in FIG. 1) may be mounted on container 19 for operating through elongated window 2. The wireless spectrometer may be any type of spectrometer 21 described above and may be mounted to elongated window 2. The wireless spectrometer is preferably mounted so as to be movable to a variety of positions along the elongated window 2. In some embodiments of the present invention a suitable track may be provided outside the rim of elongated window 2 along which the wireless spectrometer translates. Any type of translation device, such as a stepper motor, etc., may be used to move the wireless spectrometer. Any suitable control device may be used to control the motion of the wireless spectrometer. The wireless spectrometer may be locked into place along the track for taking spectral data. This embodiment of the present invention having elongated window 2 permits product 11 in a variety of locations in container 19 to be analyzed. Moreover, smaller amounts of product 11 in container 19, such as experimental batches, for example, may be advantageously analyzed using this embodiment.

In other embodiments of the present invention more than one wireless spectrometer may be mounted along elongated window 2. Moreover, where more than one window is provided a respective spectrometer may be mounted on each window.

Figure 19:
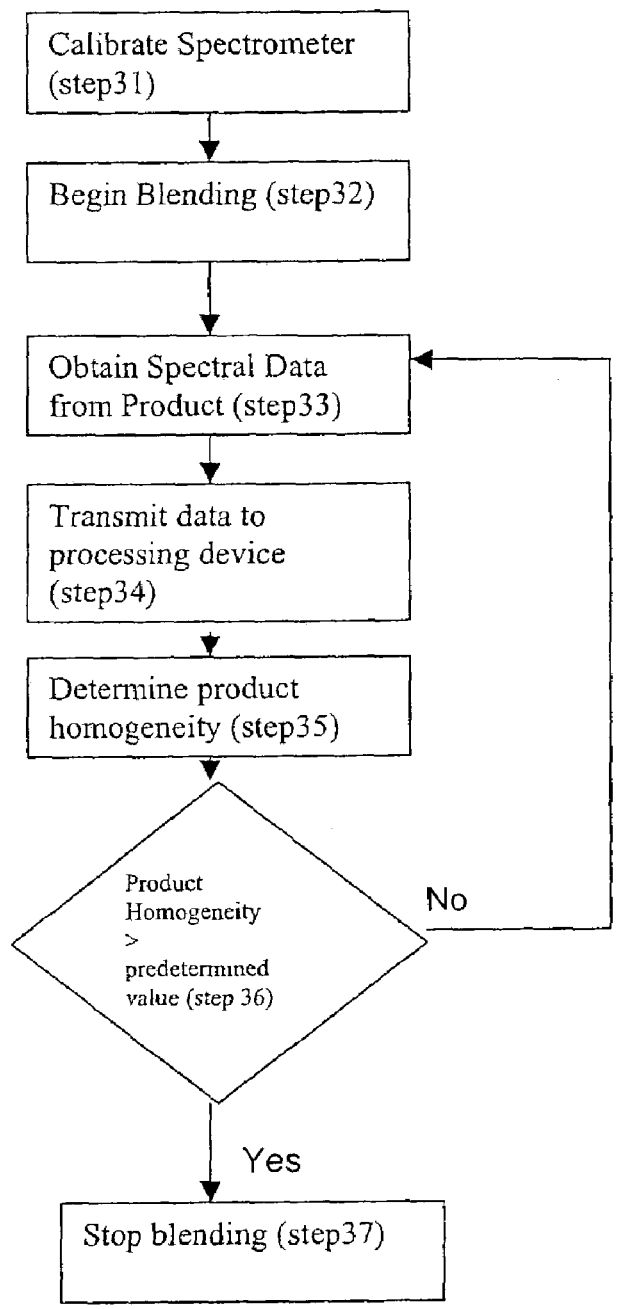
FIG. 19 shows a flow chart of a method according to the present invention.

FIG. 19 shows a flow chart of a method according to the present invention. Processing device 232 may be used to calibrate spectrometers 21 (step 31) according to what is known about the individual compositions of matter to be blended, the desired homogeneity of the blended product, specifications of spectrometers 21, etc. Once the individual compositions of matters are entered into container 19, and spectrometers 21 have been calibrated, the blending process may begin (step 32) by rotating shafts 16 and container 19 using blender driver 18. Blender driver 18 may be controlled by processing device 232. During blending, wireless spectrometers 21 operate through windows 12 and 13 to each obtain a set of spectroscopic data regarding the product (step 33). The exemplary embodiment shown in FIG. 1 includes two spectrometers each obtaining a set of spectroscopic data regarding the product, however a single spectrometer may also be used to obtain a single set of spectroscopic data. Likewise, more than two spectrometers may be used to obtain multiple sets of spectroscopic data regarding the product.

The spectrometers may transmit the sets of spectroscopic data (step 34) to processing device 232. Processing device 232 processes the sets of spectroscopic data to determine product homogeneity (step 35). Processing device 232 then compares the determined product homogeneity to a predetermined value (step 36). The predetermined value may correspond to a desired homogeneity value and may be determined according to empirical data for the blended product, the placement of the spectrometer on the container, etc. If the determined product homogeneity is not greater than the predetermined value, another set of spectral data is obtained by spectrometers 21 (step 33) and the transmitting, determining and comparison steps (steps 34 through 36) are repeated. Once the determined product homogeneity value exceeds the predetermined value, the blending stops (step 37). Advantageously, processing device 232 may stop the blending process by sending a stop signal to blender driver 18.

Thus, an apparatus for analyzing for monitoring homogeneity and detecting homogeneity of pharmaceutical components as they are being prepared in a dosage form has been disclosed. One skilled in the art will appreciate that the present invention can be carried out in other ways and practiced by other than the described embodiments. The present embodiments therefore should be considered in all respects as illustrative, and the present invention is limited only by the claims that follow.

What is claimed is:

1. An apparatus for blending a product, the apparatus comprising:
   a blender including a container having a wall, the wall including a window formed therein, the container rotating about an axis of rotation; and
   a wireless spectrometer mounted to the container and operating through the window, in a direction that does not intersect the axis of rotation, the wireless spectrometer capable of obtaining a set of spectroscopic data regarding the product during an operation of the blender.

2. The apparatus as recited in claim 1 wherein the spectrometer includes a near infrared spectrometer.

3. The apparatus as recited in claim 1 further comprising a remote processing device in communication with the spectrometer.

4. The apparatus as recited in claim 3 wherein the spectrometer communicates to the remote processing device during an operation of the blender.

5. The apparatus as recited in claim 3 wherein the remote processing device calculates a value indicative of a homogeneity of the product.

6. The apparatus as recited in claim 3 wherein the spectrometer receives calibration information from the remote processing device before obtaining spectroscopic data.

7. The apparatus as recited in claim 3 wherein the remote processing device is operatively connected to the blender, and the remote processing device ends an operation of the blender when the calculated value reaches a predetermined value.

8. The apparatus as recited in claim 1 wherein the product includes a powder.

9. The apparatus as recited in claim 1 further comprising:
a second window disposed in the wall so as not to intersect with the axis of rotation; and
a second wireless spectrometer mounted on the container operating through the second window for obtaining a second set of spectroscopic data regarding the product.

10. The apparatus as recited in claim 1, wherein said spectrometer comprises a light source for irradiating said product and at least one detector for detecting radiation reflected off or transmitted through said product.

11. The apparatus as recited in claim 10, wherein said at least one detector is on a side of said blender proximate to said light source for detecting light reflected off said product.

12. The apparatus as recited in claim 10, wherein said at least one detector is on a side of said blender remote from said light source for detecting light transmitted through said product.

13. The apparatus as recited in claim 10, wherein said light source emits radiation in multiple wavelengths, said apparatus further comprising a filter for restricting passage of light through said filter in only a specific predetermined range of wavelengths.

14. The apparatus as recited in claim 13, wherein said filter is situated between said light source and said product, such that said filtering means allows passage of light in only a specific predetermined range of wavelengths to pass to said product.

15. The apparatus as recited in claim 13, wherein said filter is situated between said product and said at least one detector, such that said filter allows passage of only a specific predetermined range of wavelengths reflected off or transmitted through said product to pass to said at least one detector.

16. The apparatus as recited in claim 13, wherein said filter is at least one linear variable filter.

17. The apparatus as recited in claim 13, wherein said at least one detector is at least one array detector.

18. The apparatus as recited in claim 13, wherein said at least one detector is at least one diode.

19. The apparatus as recited in claim 13, wherein the filter is a bandpass filter.

20. The apparatus as recited in claim 19, wherein the filter includes a plurality of bandpass filters.

21. The apparatus as recited in claim 13, wherein said filter is a grating.

22. The apparatus as recited in claim 21, wherein said grating is a diffraction grating.

23. The apparatus as recited in claim 10, wherein said light source emits light in only a specific predetermined range of wavelengths, and wherein said at least one detector detects light reflected off or transmitted through said product in said specific predetermined range of wavelengths.

24. The apparatus as recited in claim 10, wherein said light source emits light in multiple wavelengths, and wherein each of said at least one detector detects light reflected off or transmitted through said product in only a specific predetermined range of wavelengths.

25. The apparatus as recited in claim 3, wherein said spectrometer sends information regarding said spectroscopic data to said processing device through infrared radiation or near infrared radiation.

26. The apparatus as recited in claim 10, wherein said light source is capable of illuminating a plurality of positions in a region of said blender.

27. The apparatus as recited in claim 26, wherein said light source includes a fiber optic bundle for illuminating said plurality of positions.

28. The apparatus as recited in claim 27, wherein said light source includes a plurality of near-infrared light emitting diodes, each for illuminating a respective position of the plurality of positions.

29. The apparatus as recited in claim 27, wherein said at least one detector is disposed in said region for detecting light reflected off or transmitted through said product.

30. The apparatus as recited in claim 29, wherein each of said at least one detector is configured for detecting a respective wavelength of light.

31. The apparatus as recited in claim 27, further comprising:
a plurality of optical fibers spaced apart on the region for receiving radiation reflected off or transmitted through said product and delivering said respective radiation to said at least one detector; and
a switching device coupled to each of the plurality of optical fibers and to the at least one detector, the switching device configured to connect one of said respective optical fiber at a time to said at least one detector.

32. The apparatus as recited in claim 1 wherein the spectrometer is mounted to the window.

33. The apparatus as recited in claim 1 wherein the window is elongated and the spectrometer is repositionable along the window.

34. The apparatus as recited in claim 33 wherein the spectrometer is capable of being fixed in place at a plurality of positions along the window for obtaining a respective set of spectroscopic data at each position.

35. The apparatus as recited in claim 33 wherein the container has a V-shape and the window is disposed along a long axis of a leg of the container.

36. An apparatus for blending a product, the apparatus comprising:
a blender including a container having a wall, the wall including a first window and a second window disposed therein, the container rotating about an axis of rotation;
a first wireless spectrometer mounted on the container and operating through the first window, in a direction that does not intersect the axis of rotation, for obtaining a first set of spectroscopic data regarding the product during an operation of the blender;

a second wireless spectrometer mounted on the container and operating through the second window, in a direction that does not intersect the axis of rotation, for obtaining a second set of spectroscopic data regarding the product during an operation of the blender; and
a remote processing device in communication with the first and second wireless spectrometers.

37. The apparatus as recited in claim 36 wherein the wireless spectrometers include near infrared spectrometers.

38. The apparatus as recited in claim 36 wherein the first and second wireless spectrometers are capable of communicating to the remote processing device during an operation of the blender.

39. The apparatus as recited in claim 36 wherein the remote processing device calculates a value indicative of a homogeneity of the product.

40. The apparatus as recited in claim 36 wherein the first and second wireless spectrometers are capable of receiving calibration information from the remote processing device before obtaining spectroscopic data.

41. The apparatus as recited in claim 36 wherein the computer is operatively collected to the blender, and the remote processing device ends an operation of the blender when the calculated value reaches a predetermined value.

42. The apparatus as recited in claim 36 wherein the product includes a powder.

43. The apparatus of claim 1, further comprising at least one second wireless spectrometer and wherein said wireless spectrometer and each of said at least one second wireless spectrometer include a respective light source for irradiating a portion of said product at a respective position.

44. The apparatus of claim 43, wherein said wireless spectrometer and each of said at least one second wireless spectrometer are disposed at a respective position on said blender.

45. The apparatus of claim 44, wherein each of said respective position is at a respective longitudinal level of said blender so as to enable a determination of stratification in said product.

46. The apparatus of claim 43, wherein each said light source includes a respective individual optical fiber of a common fiber optic bundle light source.

47. The apparatus of claim 46, further comprising a filter device for restricting passage of light from the common fiber optic bundle light source through said filter to a predetermined wavelength or range of wavelengths.

48. The apparatus as recited in claim 9 wherein the first spectrometer is mounted to the first window and the second spectrometer is mounted to the second window.

49. A method for assaying a blended product in a blender, the blender including a container having a wall and an axis of rotation, the wall including a window, the method comprising:
mounting a wireless spectrometer to the container;
rotating the container about its axis of rotation so as to blend the product;
operating the wireless spectrometer through the window, in a direction that does not intersect the axis of rotation, to obtain spectroscopic data regarding the product during the blending; and
determining a homogeneity of the product from the spectroscopic data.

50. The method as recited in claim 49 wherein the spectrometer is a near infrared spectrometer.

51. The method as recited in claim 49 wherein the determining of the homogeneity is performed during the blending.

52. The method as recited in claim 49 further comprising transmitting the spectroscopic data to a remote processing device.

53. The method as recited in claim 52 wherein the transmitting is performed during the blending of the product.

54. The method as recited in claim 52 wherein the determining of the homogeneity is performed by the remote processing device.

55. The method as recited in claim 52 further comprising downloading calibration information to the spectrometer.

56. The method as recited in claim 49 wherein the product includes a powder.

57. The method as recited in claim 49 further comprising stopping the rotating when the homogeneity of the product reaches a predetermined value.

58. The method as recited in claim 49, further comprising the step of pre-treating, with a pre-treatment technique, the spectroscopic data.

59. The method as recited in claim 58, wherein pre-treatment technique is selected from the group consisting of: a baseline connection, a normalization of the spectroscopic data, a first derivative on the spectroscopic data, a second derivative on the spectroscopic data, a multiplicative scatter correction on the spectroscopic data, a smoothing transform on the spectroscopic data, a Savitsky-Golay first derivative, a Savitsky-Golay second derivative, a mean-centering, a Kubelka-Munk transform, and a conversion from reflectance/transmittance to absorbence.

60. The method as recited in claim 49, further comprising applying a data reduction technique to the spectroscopic data.

61. The method as recited in claim 60, wherein the data reduction technique is selected from the group consisting of: partial least squares, a neural net, a classical least squares, a principal component regression, and a multiple linear regression.

62. The method as recited in claim 59, further comprising applying a data reduction technique to the pre-treated spectroscopic data.

63. The method as recited in claim 62, wherein the data reduction technique is selected from the group consisting of a partial least squares, a neural net, a classical least squares, a principal component regression, and a multiple linear regression.

64. The method as recited in claim 49, wherein the operating the wireless spectrometer is performed so as to obtain respective spectroscopic data at at least two points in time and wherein the determining the homogeneity of the product is performed by comparing the respective spectroscopic data obtained at the at least two points in time.

65. The method as recited in claim 49, wherein the mounting the wireless spectrometer to the container is performed by mounting the wireless spectrometer to the window.

66. The method as recited in claim 49, wherein the window is elongated and wherein the operating the wireless spectrometer through the window is performed by repositioning the wireless spectrometer at a plurality of positions along the window and obtaining respective spectroscopic data at each position.

67. A method for assaying a blended product in a blender, the blender including a container having a wall and first and second windows disposed in the wall and an axis of rotation, the method comprising:
blending the product in the blender;

operating a first and a second wireless spectrometer through the respective first and second windows, each in a respective direction that does not intersect the axis of rotation, to obtain a respective first and second sets of spectroscopic data regarding the product; and determining a homogeneity of the product from the first and second sets of spectroscopic data.

68. The method as recited in claim 67 wherein the spectrometers are near infrared spectrometers.

69. The method as recited in claim 67 wherein the determining of the homogeneity is performed during the blending.

70. The method as recited in claim 67 further comprising transmitting the spectroscopic data to a remote processing device.

71. The method as recited in claim 67 wherein the transmitting is performed during the blending of the product.

72. The method as recited in claim 70 wherein the determining of the homogeneity is performed by the remote processing device.

73. The method as recited in claim 67 further comprising downloading calibration information to the spectrometer.

74. The method as recited in claim 67 wherein the product includes a powder.

75. The method as recited in claim 67 further comprising stopping the rotating when the homogeneity of the product reaches a predetermined value.

76. The method as recited in claim 67 further comprising mounting the first spectrometer to the first window and the second spectrometer to the second window.

77. An apparatus for blending a product, the apparatus comprising:
- a blender including a container having a wall, the wall including a window formed therein, the container rotating about an axis of rotation;
- a wireless spectrometer mounted to the container and operating through the window, in a direction that does not intersect the axis of rotation, the wireless spectrometer capable of obtaining a set of spectroscopic data regarding the product during an operation of the blender, said spectrometer comprising a light source emitting radiation in multiple wavelengths for irradiating said product and at least one detector for detecting radiation reflected off or transmitted through said product;
- at least one linear variable filter for restricting passage of light through said filter in only a specific predetermined range of wavelengths; and
- a solid state translation device operatively connected to said at least one linear variable filter and configured for moving said at least one linear variable filter.

78. The apparatus as recited in claim 77, wherein said at least one detector comprises a plurality of individual detectors.

79. The apparatus as recited in claim 77, wherein said solid state translation device is a piezoelectric bimorph.

80. The apparatus as recited in claim 79, further comprising a lever device coupling said piezoelectric bimorph to said at least one linear variable filter and configured for amplifying a movement of said at least one linear variable filter relative to a movement of said piezoelectric bimorph.

* * * * *